(12) United States Patent
Anro et al.

(10) Patent No.: US 8,710,021 B2
(45) Date of Patent: Apr. 29, 2014

(54) INHIBITION OF HRP-3 USING MODIFIED OLIGONUCLEOTIDES

(75) Inventors: Valentina Anro, Montalto Dora (IT); Sarah Dewilde, Lessolo (IT); Domenico Barone, Turin (IT); Nicoletta Minari, Biella (IT); Enrico M. Bucci, Ivrea (IT); Roberto Sapio, Bellizzi (IT); Margherita Valente, Formia (IT); Sara Tosti, Camburzano (IT); Laura Ricci, Burolo (IT)

(73) Assignee: Bionucleon S.r.l., Colleretto Giacosa (TO) (IT)

( * ) Notice: Subject to any disclaimer, the term of this patent is extended or adjusted under 35 U.S.C. 154(b) by 181 days.

(21) Appl. No.: 12/997,720

(22) PCT Filed: Jun. 10, 2009

(86) PCT No.: PCT/EP2009/004186
§ 371 (c)(1),
(2), (4) Date: Apr. 18, 2011

(87) PCT Pub. No.: WO2009/149921
PCT Pub. Date: Dec. 17, 2009

(65) Prior Publication Data
US 2011/0190445 A1 Aug. 4, 2011

Related U.S. Application Data

(60) Provisional application No. 61/060,571, filed on Jun. 11, 2008.

(51) Int. Cl.
C07H 21/02 (2006.01)
C07H 21/04 (2006.01)
A61K 31/70 (2006.01)
C12N 15/113 (2010.01)
C12Q 1/68 (2006.01)

(52) U.S. Cl.
CPC .......... *C12N 15/113* (2013.01); *C12N 2310/14* (2013.01)
USPC ....... 514/44 A; 536/23.1; 536/24.1; 536/24.5; 435/6.1; 435/375; 435/377

(58) Field of Classification Search
None
See application file for complete search history.

(56) References Cited

U.S. PATENT DOCUMENTS

| 6,893,844 | B1 | 5/2005 | Yu et al. | |
|---|---|---|---|---|
| 7,141,375 | B2 * | 11/2006 | Pietras et al. | 435/6.11 |
| 7,998,939 | B2 * | 8/2011 | Diener et al. | 514/44 R |
| 8,193,159 | B2 * | 6/2012 | Purschke et al. | 514/44 R |
| 8,314,223 | B2 * | 11/2012 | Purschke et al. | 536/23.1 |
| 8,367,629 | B2 * | 2/2013 | Purschke et al. | 514/44 R |

FOREIGN PATENT DOCUMENTS

| EP | 1 526 177 A1 | | 4/2005 |
|---|---|---|---|
| WO | WO 94/01550 | * | 1/1994 |
| WO | 0190155 A2 | | 11/2001 |
| WO | 2004015075 A2 | | 2/2004 |
| WO | 2005026334 A2 | | 3/2005 |
| WO | WO 2005/111238 | * | 11/2005 |
| WO | 2006/002971 A2 | | 1/2006 |
| WO | 2008/054431 A2 | | 5/2008 |

OTHER PUBLICATIONS

Gao H et al: "Double-stranded cyclic oligonucleotides with non-nucleotide bridges." Bioconjugate Chemistry Sep.-Oct. 1994, vol. 5, No. 5, Sep. 1994, pp. 445-453, XP002549926.
Lukasik Stephen M et al: "High resolution structure of the HDGF PWWP domain: a potential DNA binding domain." Protein Science : A Publication of the Protein Society Feb. 2006, vol. 15, No. 2, Feb. 2006, pp. 314-323, XP002549927 ISSN: 0961-8368 cited in the application p. 319, right-hand column; figure 3.
Ortega-Paino Eva et al: "Functionally associated targets in mantle cell lymphoma as defined by DNA microarrays and RNA interference." Blood Feb. 1, 2008, vol. 111, No. 3, Feb. 1, 2008, pp. 1617-1624, XP002550066 ISSN: 0006-4971.
Kishima Yoshihiko et al: "Antisense oligonucleotides of hepatoma-derived growth factor (HDGF) suppress the proliferation of hepatoma cells." Hepato-Gastroenterology Nov.-Dec. 2002, vol. 49, No. 48, Nov. 2002, pp. 1639-1644, XP009124141 ISSN: 0172-6390.
Zhang Jun et al: "Down-regulation of hepatoma-derived growth factor inhibits anchorage-independent growth and invasion of non-small cell lung cancer cells." Cancer Research Jan. 1, 2006, vol. 66, No. 1, Jan. 1, 2006, pp. 18-23, XP002550054 ISSN: 0008-5472.
Nameki N et al: "Solution Structure of the PWWP Domain of the Hepatoma-Derived Growth Factor Family" Protein Science, vol. 14, No. 3, Mar. 1, 2005, pp. 756-764, XP009059711 Cambridge University Press, Cambridge, GB ISSN: 0961-8368.
Yang Jun et al: "Hepatoma derived growth factor binds DNA through the N-terminal PWWP domain" BMC Molecular Biology, vol. 8, No. 1, Oct. 31, 2007, p. 101, XP021033406 Biomed Central Ltd, GB ISSN: 1471-2199—& Yang Jun et al: "Additional Data 2 (Hepatoma derived growth factor binds DNA through the N-terminal PWWP domain)" BMC Molecular Biology, Oct. 31, 2007, XP002549929 Retrieved from the Internet: URL:http://www.biomedcentral.com/1471-2199/8/101/additional/> [retrieved on Oct. 12, 2009] [retrieved on Nov. 28, 2006].
Bucci EM et al.: "More than antisense. Targeting extracellular proteins by oligonucleotide analogues" Screening Trends in Drug Discovery, vol. 02, 2006, pp. 32-33, XP002549928 Darmstadt, Germany.
Hosoya T et al: "Sequence-specific inhibition of a transcription factor by circular dumbbell DNA oligonucleotides" FEBS Letters, vol. 461, No. 3, Nov. 19, 1999, pp. 136-140, XP004260536 Elsevier, Amsterdam, NL ISSN: 0014-5793.
Kim S H et al: "PEG conjugated VEGF siRNA for anti-angiogenic gene therapy" Journal of Controlled Release, vol. 116, No. 2, Nov. 28, 2006, pp. 123-129, XP024957696 Elsevier, Amsterdam, NL ISSN: 0168-3659.

(Continued)

*Primary Examiner* — Sean McGarry
(74) *Attorney, Agent, or Firm* — Rothwell, Figg, Ernst & Manbeck, P.C.

(57) ABSTRACT

The present invention refers to agents for modulating the activity of proteins having a PWWP domain.

26 Claims, 24 Drawing Sheets

(56) References Cited

OTHER PUBLICATIONS

Jones D S et al: "Conjugates of Double-Stranded Oligonucleotides With Poly(Ethylene Glycol) and Keyhole Limpet Kemocyanin: A Model for Treating Systemic Lupus Erytematosus" Bioconjugate Chemistry, vol. 5, No. 5, Sep. 1, 1994, pp. 390-399, XP000465950 ACS, Washington, DC, US ISSN: 1043-1802.

Jaschke A et al: "Synthesis and properties of oligodeoxyribonucleotide polyethylen glycol conjugates" Nucleic Acids Research, vol. 22, No. 22, Jan. 1, 1994, pp. 4810-4817, XP008098272 Oxford University Press, Surrey, GB ISSN: 0305-1048.

Suzuki Hiromitsu et al: "Decreased expression of the SIN3A gene, a candidate tumor suppressor located at the prevalent allelic loss region 15q23 in non-small cell lung cancer." Lung Cancer (Amsterdam, Netherlands) Jan. 2008, vol. 59, nd. 1, Jan. 2008, pp. 24-31, XP022408365 ISSN: 0169-5002 p. 26, right-hand column.

L'Esperance Sylvain et al: "Global gene expression analysis of early response to chemotherapy treatment in.ovarian cancer spheroids." BMC Genomics 2008, vol. 9, Feb. 26, 2008, p. 99, XP002564295 ISSN: 1471-2164 tables 2,5,6.

Spira Avrum et al: "Airway epithelia gene expression in the diagnostic evaluation of smokers with suspect lung cancer." Nature Medicine Mar. 2007, vol. 13, No. 3, Mar. 2007, pp. 361-366, XP002503693 ISSN: 1078-8956 figure 2.

Duale Nur et al: "Molecular portrait of cisplatin induced response in human testis cancer cell lines based on gene expression profiles." Molecular Cancer 2007, vol. 6, 2007, p. 53, XP002564296 ISSN: 1476-4598 figure 1.

Abba Martin C et al: "Gene expression signature of estrogen receptor alpha status in breast cancer." BMC Genomics 2005, vol. 6, No. 1, 2005, p. 37, XP021002300 ISSN: 1471-2164 tables 1,2.

Notification of Reasons for Refusal in Japanese Patent Application No. 2011-512892 dispatched Dec. 16, 2013 (Translation), 7 pages.

\* cited by examiner

HRP3 mRNA expression

Figure 12

Duplex 1
SEQ ID NO 8   5'- TAC AAC ACC CAC AAA - 3'
SEQ ID NO 9   3'- ATG TTG TGG GTG TTT - 5'

Duplex 2
SEQ ID NO 10   5'- TAC AAC A<u>TT</u> CAC AAA - 3'
SEQ ID NO 11   3'- ATG TTG <u>TAA</u> GTG TTT - 5'

Duplex 3
SEQ ID NO 12   5'- TAC AAC <u>AA</u> ACC CAC AAA - 3'
SEQ ID NO 13   3'- ATG TTG .. TGG GTG TTT - 5'

Duplex 4
SEQ ID NO 14   5'- <u>CAC ACA CAC ACA CAC</u> - 3'
SEQ ID NO 15   3'- <u>GTG TGT GTG TGT GTG</u> - 5'

Relative quantity of HRP-3 mRNA (Real Time PCR)

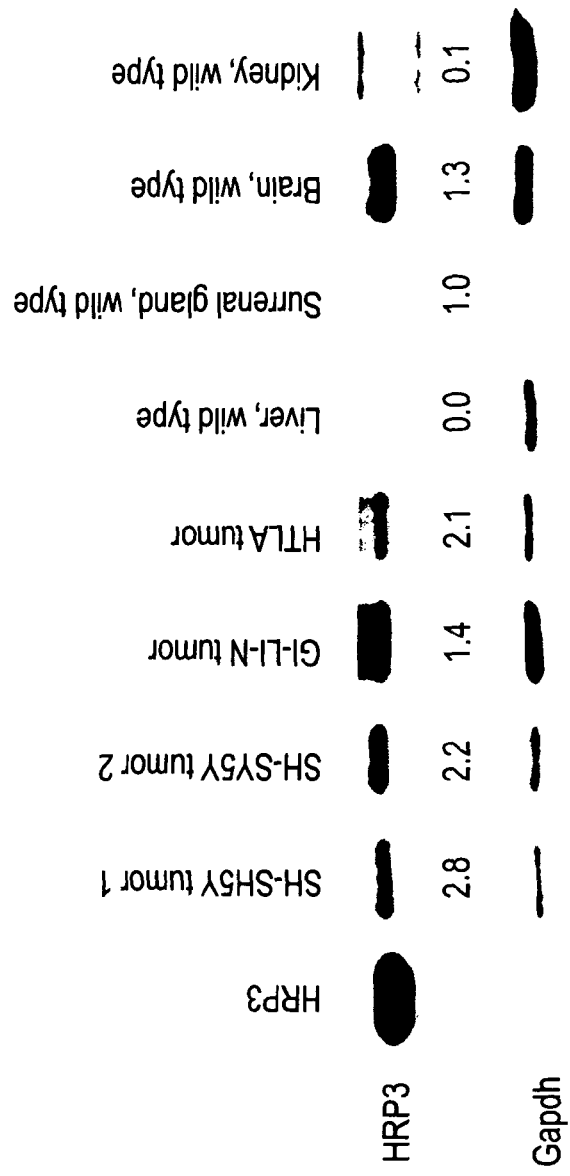

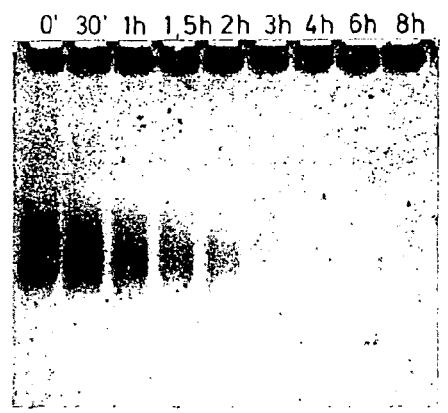# BN 203
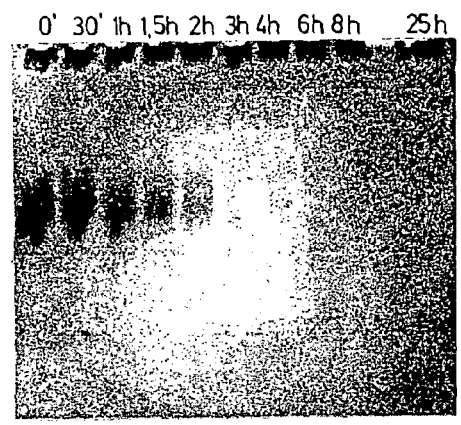# BN 204
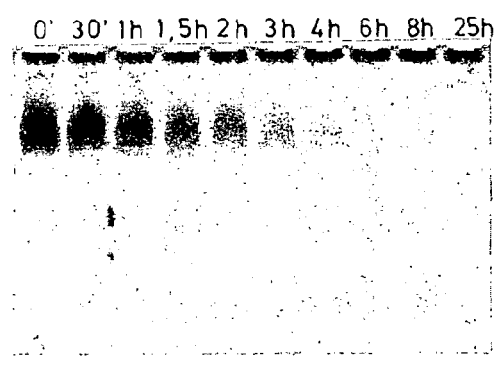# BN 205
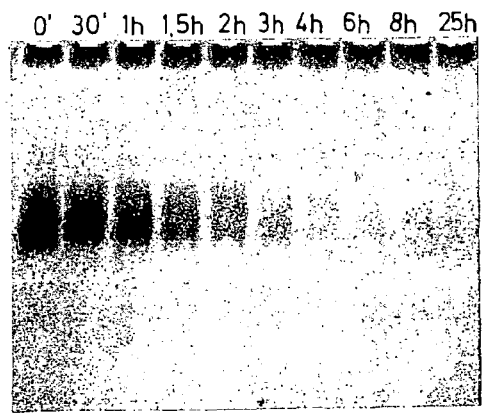# BN 206
Figure 15

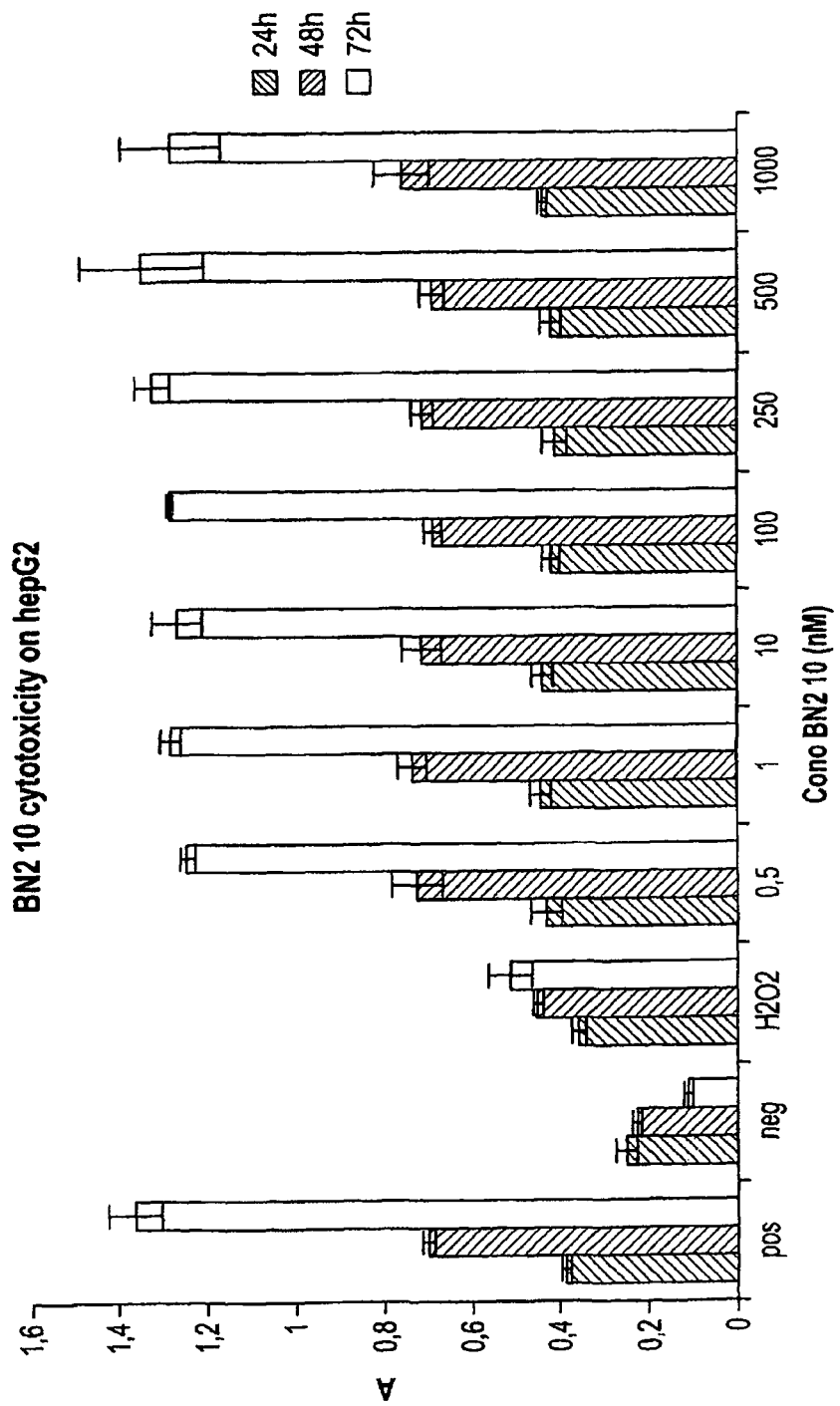

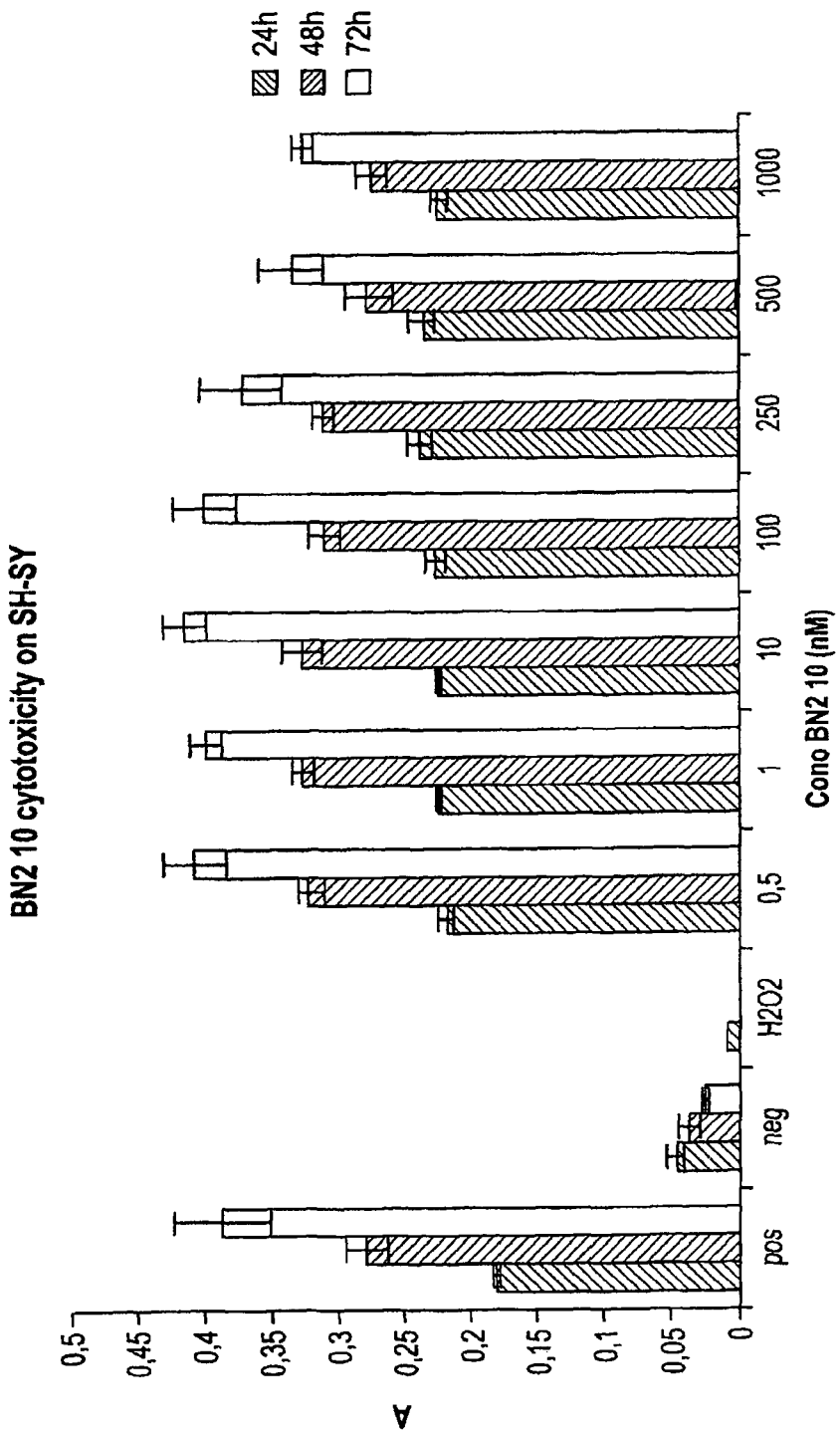

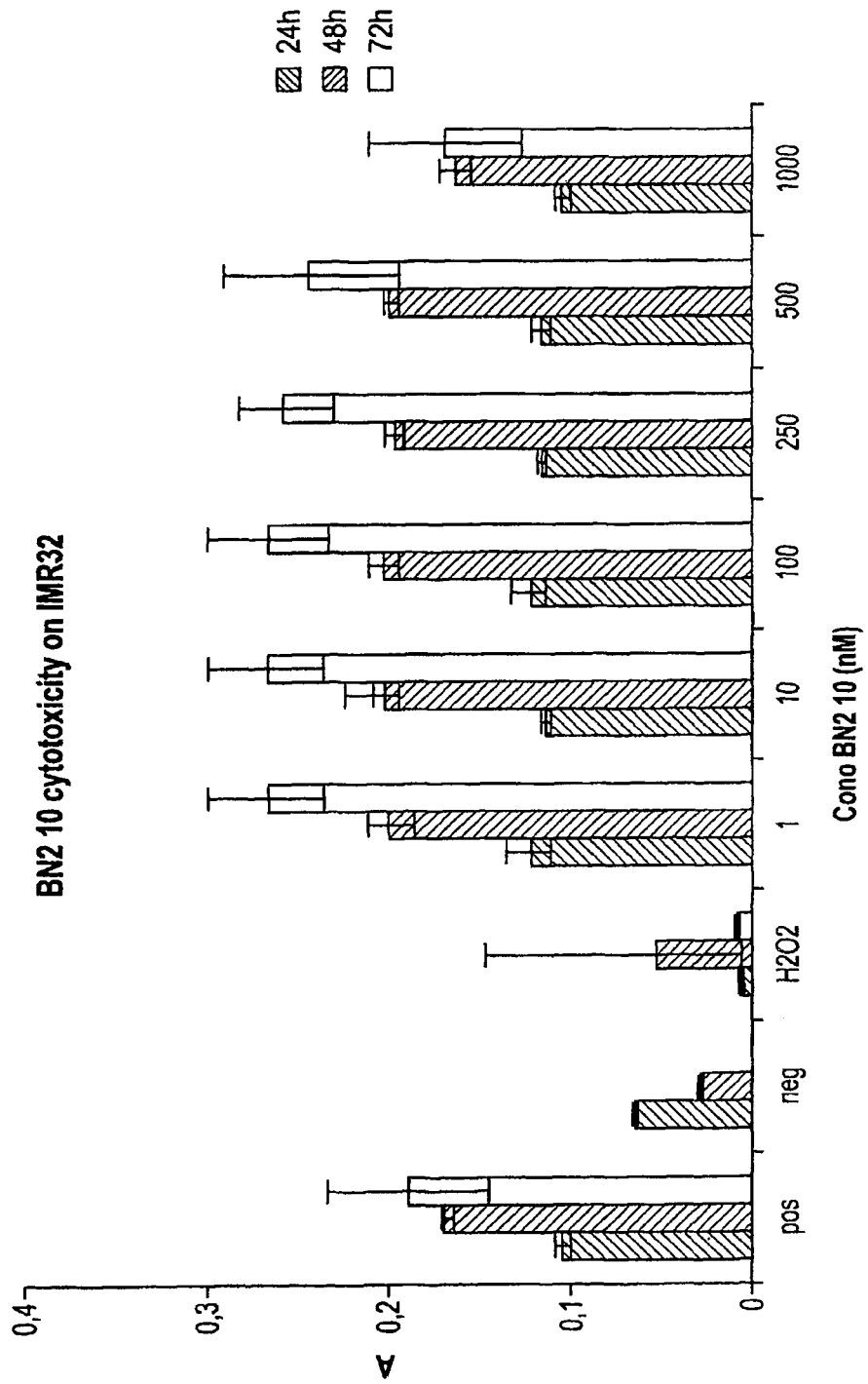

INHIBITION OF HRP-3 USING MODIFIED OLIGONUCLEOTIDES

CROSS REFERENCE TO RELATED APPLICATION

This application is a 35 U.S.C. 371 National Phase Entry Application from PCT/EP2009/004186, filed Jun. 10, 2009, which claims the benefit of U.S. Provisional Application No. 61/060,571 filed on Jun. 11, 2008, the disclosure of which is incorporated herein in its entirety by reference.

The present invention refers to agents for modulating the activity of proteins having a PWWP domain.

The PWWP domain is a conserved structural motif found in a family of proteins known as "HDGF family". This family comprises 6 proteins: HDGF, the archetypical protein; HRP-1, HRP-2, HRP-3, HRP-4 (HRP=HDGF Related Protein); and LEDGF. FIG. 1 shows the alignment of the 6 proteins and the structural conservation of the PWWP domain, which is always located to the N-terminus of all the family members. Moreover, it is also highlighted the structural homology between the PWWP domain and the oligonucleotide binding domain of two unrelated proteins; this homology points to a putative conserved role in oligonucleotide binding. This conclusion was recently supported by the NMR elucidation of the structure of a complex between the PWWP domain of HRP-3 and a duplex DNA, which confirmed the ability of the PWWP domain to bind at least a ds DNA, with micromolar (μM) affinity. The fact that the PWWP domain is able to bind oligonucleotides paves the way to the targeting of the proteins in the HDGF family by short oligonucleotides for therapeutical and diagnostic uses.

The present inventors have identified novel biological activities of PWWP domain proteins. Particularly, it was found that HRP-3 is capable of inhibiting migration, proliferation and/or anchorage independent growth of NIH 3T3 cells. Further it was found that HRP-3 acts as an angiogenesis-promoting agent on HUVEC-cells. Furthermore, it was found that HRP-3 is overexpressed in neural tumors, particularly in neuroblastoma cells. Finally, the inventors have identified novel single-stranded oligonucleotide molecules capable of binding to the PWWP domain with high affinity and thus capable of inhibiting the activity of PWWP domain proteins.

A first aspect of the present invention refers to a single-stranded oligonucleotide molecule capable of binding to PWWP domain proteins and capable of inhibiting and/or blocking biological effects induced by PWWP domain proteins such as HRP-3 and HDGF.

A subject-matter of the present invention is a single-stranded oligonucleotide molecule comprising the sequence

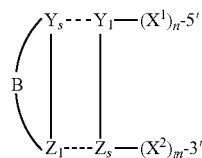

wherein Y and Z represent nucleotide or nucleotide analogue building blocks,
wherein each Y and Z form base pairs with each other, particularly Watson-Crick base pairs, $X^1$ and $X^2$ are independently selected from moieties comprising poly(alkylene glycol) units, n and m independently represent 0 or 1 wherein at least one of n and m is 1,
s is an integer between 1 and 20, preferably between 5 and 18,
and B is a bridging moiety.

Preferably, the present invention refers to a single-stranded oligonucleotide molecule comprising the sequence

```
                                      (SEQ ID NO. 1)
5'-(X¹)ₙ-TAC AAC ACC CAC AAA-B-TTT GTG GGT GTT GTA-
(X²)ₘ-3'
``` wherein A, C, T and G represent nucleotide or nucleotide analogue building blocks, $X^1$ and $X^2$ are independently selected from moieties comprising poly(alkylene glycol) units, n and m independently represent 0 or 1, wherein at least one of n and m is 1, and B represents a bridging moiety.

The oligonucleotide molecule comprises nucleotide or nucleotide analogue building blocks capable of forming base pairs with each other, particularly Watson-Crick base pairs. Preferably, the building blocks are selected from "A", "C", "T" and "G". The "A" building blocks are selected from building blocks comprising the nucleobase adenine or an analogue thereof capable of forming a base pair with a complementary nucleobase "T". The "C" building blocks are selected from building bocks containing the nucleobase cytidine or an analogue thereof capable of forming a base pair with a complementary nucleobase "G". The "T" building blocks comprise the nucleobase thymine or analogues thereof, including the nucleobase uracil (alternately also identified as "U" building block), capable of forming a base pair with a complementary nucleobase "A", and the "G" building blocks comprise the nucleobase guanine or analogues thereof capable of forming a base pair with a complementary nucleobase "C".

The building blocks A, C, T and G are preferably selected from deoxyribonucleotide building blocks, modified deoxyribonucleotide building bocks, ribonucleotide building blocks, modified ribonucleotide building blocks, nucleotide analogue building blocks, particularly PNA, LNA or morpholino building blocks or combinations thereof. Examples of modified deoxyribonucleotide or ribonucleotide building blocks are nucleotides wherein the 2'-C-atom of the ribose sugar is substituted with halogen, e.g. F, Cl, Br or I, cyano, alkyl, e.g. $C_1$-$C_6$ alkyl, alkenyl, e.g. $C_2$-$C_6$ alkenyl, alkynyl, e.g. $C_2$-$C_6$ alkynyl, amino, mono- or di-alkyl substituted amino, e.g. $C_1$-$C_6$ alkyl amino, alkoxy, e.g. $C_1$-$C_6$ alkoxy, wherein alkyl, alkenyl and alkynyl groups may be unsubstituted or mono- or polysubstituted by halogen, hydroxy- or alkoxy-groups. Further examples of building blocks are oligonucleotide analogues with modifications that take place on the phosphorus atom of the sugar-phosphate backbone, e.g. phosphorothioates, methyl phosphonates, phosphoramidates and phosphotriesters (e.g. Cohen, J. S., ed. Oligonucleotides: Antisense Inhibitors of Gene Expression, (CRC Press, Inc., Boca Raton Fla., 1989). Preferred examples include peptide Nucleic Acids, (PNA), hydroxyproline peptide nucleic acids (HypNA), Serine peptide nucleic acids (SerNA) (e.g. WO 2001/068673—Oligonucleotide Analogues, method of synthesis and method of use). Morpholino and heterocyclic analogues, 2'-modified nucleosides, e.g. 2'F RNA or 2'OMe RNA, conformationally restricted nucleotides bi, tri, or polycyclic nucleoside analogues, e.g. a-bicyclo-DNA, 8-bicyclo-DNA 5',6'bicyclo-DNA, Locked Nucleoside Analogues (LNA), and analogues including spiro moieties (cf. as described by Velazquez S, San Felix A, Perez-Perez M J, Balzarini J, De Clercq E, Camarasa M J. *Int Conf AIDS*. 1992

Jul. 19-24; 8: Spain), oligonucleotidic analogues with thermolabile protecting groups, e.g. the 4-methylthio-1-butyl group as prodrugs (cf. as described by Beaucage S L, Curr Protoc Nucleic Acid Chem. 2004 December; Chapter 3: Unit 3.11), 2'-5' linked oligonucleotides, or oligonucleotides with 5'-5' or 3'-3' linkages (linkage inversion, through use of reversed amidites).

Very preferred building blocks A, C, T and G are selected from deoxyribonucleotide building blocks, ribonucleotide building blocks, modified ribonucleotide building blocks, preferably 2'-OMe ribonucleotide building blocks and reversed ribonucleotide building blocks forming a 3'-3' linkage inversion.

The single-stranded oligonucleotide molecules of the present invention comprise a moiety $X^1$ and/or a moiety $X^2$ located at the 5'- and 3'-termini of the molecule, respectively. In one embodiment, the oligonucleotide molecule comprises both $X^1$ and $X^2$ moieties. In a further embodiment the molecule comprises only an $X^1$ moiety and in a still further embodiment only an $X^2$ moiety.

The moieties $X^1$ and $X^2$ are selected from moieties capable of stabilizing the oligonucleotide molecule. Preferably, $X^1$ and $X^2$ are selected from moieties comprising linear or branched poly($C_2$-$C_3$-alkylene glycol) units, particularly poly(ethylene glycol) units. These units preferably have a molecular weight in the range between 200 and 100,000 Da, more preferably between 300 and 50,000 Da. In a very preferred embodiment, the poly(ethylene glycol) unit is a branched poly(ethylene glycol) unit with two poly(ethylene glycol) chains of each 20 kDa, i.e. a branched poly(ethylene glycol) unit with a molecular weight of 40,000 Da (PEG (40 KDa)).

Further, the oligonucleotide molecule of the present invention comprises a bridging unit B providing a scaffold, which allows the formation of a double-stranded stem structure between the 5'- and 3'-self-complementary oligonucleotide units within the molecule. The length of the bridging unit is preferably 1-20 nucleotidic or non-nucleotidic building blocks. Preferably, the bridging unit comprises (i) a nucleotidic spacer sequence of at least 3 unpaired nucleotide or nucleotide analogue building blocks, or (ii) a non-nucleotidic spacer sequence, e.g. a poly(ethylene glycol) spacer sequence of at least 3 ethylene glycid units, preferably of at least 5 ethylene glycol units.

More preferably, the bridging unit comprises 3 "A" building blocks, e.g. the deoxyribonucleotide sequence AAA or a poly(ethylene glycol) spacer sequence comprising 3-10, preferably 5-10, e.g. 3, 5, 7 or 10 ethylene glycol units. More preferably the 3 "A" building blocks of the bridging unit comprise 2'OMe modified ribonucleotide building blocks, e.g. the modified ribonucleotide sequence AAA(2'-OMe).

The oligonucleotide molecule of the present invention is preferably capable of inhibiting PWWP domain proteins e.g. HDGF, HDGF-2, HRP-1, HRP-2, HRP-3, HRP-4 and/or LEDGF, particularly HRP-3 and/or HDGF. The PWWP domain is preferably as defined in Prosite PS50821, Pfam PF00855 or InterPRO IPRO00313.

The PWWP domain proteins are preferably mammalian proteins, more preferably human proteins, e.g. human HDGF (Swiss Prot. No. P51858/Q7Z4S4/Q7Z4S5), human HDGF-2 (Swiss Prot. No. Q7Z4V5), human HRP-3 (Swiss Prot. No. Q9Y3E1), and/or human LEDGF (Swiss Prot. No. O75475). The oligonucleotide molecule of the invention is preferably capable of inhibiting biological activities of PWWP domains such as pro-angiogenetic activity.

In a preferred embodiment, the oligonucleotide binds to a PWWP domain protein with an affinity of at least 10 µM, preferably of at least 100 µM and more preferably of at least 1000 µM. In a further preferred embodiment, the oligonucleotide binds to a PWWP domain protein with an affinity of at least 10 nM, preferably of at least 100 nM and more preferably of at least 1000 nM. The binding of the oligonucleotide to the protein may be determined by Biacore systems, circular dichroism or electrophoresis techniques, e.g. capillary electrophoresis.

The oligonucleotide molecule of the present invention may be used in medicine, e.g. in human or veterinary medicine, for diagnostic and/or therapeutic applications. For example, the oligonucleotide molecule may be used in the diagnosis and therapy of conditions or disorders associated with, accompanied by and/or caused by a PWWP domain protein dysfunction, particularly a PWWP domain protein overexpression and/or overactivity. More preferably, the oligonucleotide molecule is for use in the diagnosis and therapy of angiogenesis-related disorders such as cancers, e.g. neural cancers such as neuroblastoma, melanoma, colorectal cancer, pancreatic cancer, gastric cancer, hepatocellular cancer and lung cancer. In an especially preferred embodiment, the oligonucleotide is for use in inhibiting and/or blocking the biological activity of HRP-3, e.g. in neural cancers such as neuroblastoma.

The oligonucleotides of the invention may be administered to subjects in need thereof as a pharmaceutical composition which may comprise the active agent and pharmaceutically acceptable carriers, diluent and/or adjuvants. The pharmaceutical composition may be in any suitable form for e.g. parenteral, topical, pulmonal administration etc. Preferably, the pharmaceutical composition is suitable for parenteral administration, e.g. by injection or infusion.

The pharmaceutical composition is administered to a subject in need thereof in a therapeutically effective dose, e.g. 0.001-1000 mg or more per day depending on the type and severity of disease and the route of administration.

The oligonucleotide molecules of the present invention may be administered as a monotherapy or in combination with further therapies, e.g. irradiation, surgery and/or administration of further medicaments, e.g. anti-cancer medicaments such as chemotherapeutic agents and/or anti-tumor antibodies. Preferred examples of chemotherapeutic agents are tubulin stabilizers, tubulin destabilizers, anti-metabolites, purine synthesis inhibitors, nucleoside analogs, DNA alkylating agents, DNA modifying agents, and vascular disrupting agents. Specific examples of chemotherapeutic agents are aminoglutethimide, aminopterin, anastrozole, ancitabine, bimolane, 5-bromouracil, camptothecine, carboplatin, carmustine, chlorambucil, chlormethine, cisplatin, clodronate disodium, cyclophosphamide, cytarabine, dacarbazine, doxorubicin, ethyliminum, etoposide, floxuridine, 5-fluorouracil, flutamide, ftorafur, hydroxyurea, isophosphamide, lomustine, mercaptopurine, methotrexate, mitomycin, nitrocaphane, polyactin A, tamoxifen, thio-TEPA, calicheamycin, taxol, gemcitabine, vinblastin, vincristine, daunorubicin, docetaxel, irinotecan, epothilone B, and epothilone D. Preferred examples of anti-tumor antibodies are anti-VEGFR antibodies such as Avastin®, or other antibodies such as Herceptin®, Rituxan®, Mylotarg® and Campath®.

According to a very preferred aspect of the invention, the oligonucleotide molecules may be administered in combination with further chemotherapeutic medicaments and very preferably in combination with vincristine.

Further, the oligonucleotide molecules of the present invention may be used for drug screening e.g. to identify compounds which modulate, i.e. stimulate or inhibit the interaction of the oligonucleotide molecules and their target proteins.

A further aspect of the present invention refers to an HRP-3 polypeptide, particularly a mammalian HRP-3 polypeptide, more particularly a human HRP-3 polypeptide, or a nucleic acid molecule coding therefor for use in medicine, e.g. for diagnostic and/or therapeutic applications. This aspect is based on the finding that HRP-3 is a potent extracellular inhibitor of cellular migration, proliferation and/or anchorage independent growth of mammalian cells, particularly mammalian fibroblasts such as NIH 3T3 cells (i.e. primary mouse embryonic fibroblast cells cultured by the 3T3 protocol).

In this embodiment, the HRP-3 polypeptide may be directly administered to a subject in need thereof, e.g. a human patient. Alternatively, a nucleic acid molecule encoding a HRP-3 polypeptide may be administered by using non-viral or viral vector systems known in the art. It is preferred that the HRP-3 polypeptide or nucleic acid molecule coding thereof is administered by a protocol which allows extracellular presentation of the active agent.

A still further embodiment of the present invention relates to an HRP-3 antagonist for use in medicine, e.g. for diagnostic and/or therapeutic applications. This embodiment is based on the finding that HRP-3 has potent pro-angiogenetic activity in HUVEC-cells.

The HRP-3 polypeptide antagonist may be an antibody or an antibody fragment, e.g. a monoclonal, chimeric humanized, human or recombinant antibody or an antigen-binding fragment thereof directed against HRP-3. Alternatively, the antagonist may be a nucleic acid effector molecule, e.g. an antisense molecule, a ribozyme, an RNA interference agent, e.g. a siRNA molecule capable of inhibiting and/or blocking HRP-3 expression, or a single-stranded oligonucleotide molecule as described above. Alternatively, the antagonist may be an aptamer, e.g. a nucleic acid molecule selected to bind to the HRP-3 protein and inhibit or block its activity.

HRP-3 antagonists are administered to subjects in need thereof in the form of a pharmaceutical composition which comprises the active agent in a therapeutically effective dose. Protocols for administering the antibodies, nucleic acid effector molecules and aptamers are known in the art.

The agents of the present invention as described above are particularly useful for inhibiting angiogenesis, particularly in the diagnosis and/or therapy of angiogenesis-related conditions or disorders, and/or in the diagnosis and therapy of hyperproliferative conditions or disorders. More particularly, the agents of the present invention are useful for diagnosis and therapy in angiogenesis-related pathologies, e.g. cancer, particularly neural cancers, such as neuroblastoma, hepatoma, non small cell lung cancer (NSCLC) or neurological cancers. Further preferred areas of use include ophthalmology, pain, cardiovascular diseases, dermatology, infectious diseases, e.g. viral diseases, inflammatory and autoimmune diseases, and respiratory diseases.

Further, the present invention shall be explained in more detail by the following figures and examples.

BRIEF DESCRIPTION OF THE DRAWINGS

FIG. 12 shows the sequence of the designed duplex DNA, with the red and underlined bases in Duplex 2, 3 and 4 highlighting the changes introduced with the duplex of Lukasik et al. (Duplex 1).

FIG. 14-B) shows the expression and secretion of HRP-3 by neuroblastoma and non-neuroblastoma cells. Proteins were extracted from cell lysates or concentrated and precipitated from the conditioned medium, fractionated on SDS-PAGE gel and immunoblotted for HRP-3. Levels of GAPDH were measured for sample normalization. Relative intensity of the bands was calculated using ImageJ software.

FIG. 14-C) shows HRP-3 protein levels of SH-SH5Y, GI-LI-N and HTLA230 neuroblastoma xenografts. Proteins extracted from xenograft tumor tissues or normal mouse tissues were separated by SDS-PAGE and immunoblotted for HRP-3. Purified HRP-3 protein was used as positive control. Protein levels of GAPDH were used for sample normalization. Quantification of the bands was carried out using ImageJ software.

FIG. 15 shows the gel electrophoreses analysis of inventive oligonucleotide molecules of sequence SEQ ID No. 19, 20, 21, and 22 (indicated as compounds BN203, BN204, BN205 and BN206, respectively) after incubation in mouse serum at 37° C. for 0-25 hours.

FIGS. 16A, 16B, 16C and 16D show the cytotoxicity assay of oligonucleotide molecule of SEQ ID NO. 26 (indicated as compound BN210). MTT test was performed on HepG2 and neuroblastoma cell lines GI-L-IN,SH-SY and IMR32 after 24, 48 and 72 hrs of incubation with BN210 or control test substances. Positive and negative controls were performed using cell media containing 10% or 0% bovine serum respectively.

EXAMPLES

Material and Methods

HRP-3 Protein Source

The protein was initially obtained from a commercial source as GST conjugate. At the same time, the c-DNA was obtained from human cells by RT-PCR. The HRP-3 coding region was cloned into the pET30 vector using EcoRI and NdeI as restriction sites. The recombinant protein was produced in *E. Coli* TOPF10 and 12 positive clones were obtained. We sequenced two of positive clones to ascertain its correctness and both are correct. So we transformed our positive clones in *E. Coli* BL21 for the protein expression step. After some expression assays of ours clones in different condition of temperature and time, HRP-3 has been purified for the first step with cationic exchange by HPLC and for the second step with hydrophobic purification. After that the recombinant protein has been completely purified, we performed LAL test to verify endotoxin absence and than we quantified it.

Example 1

HRP-3 as Anti-Migrative Agent for NIH 3T3 Fibroblasts

Figure 1:
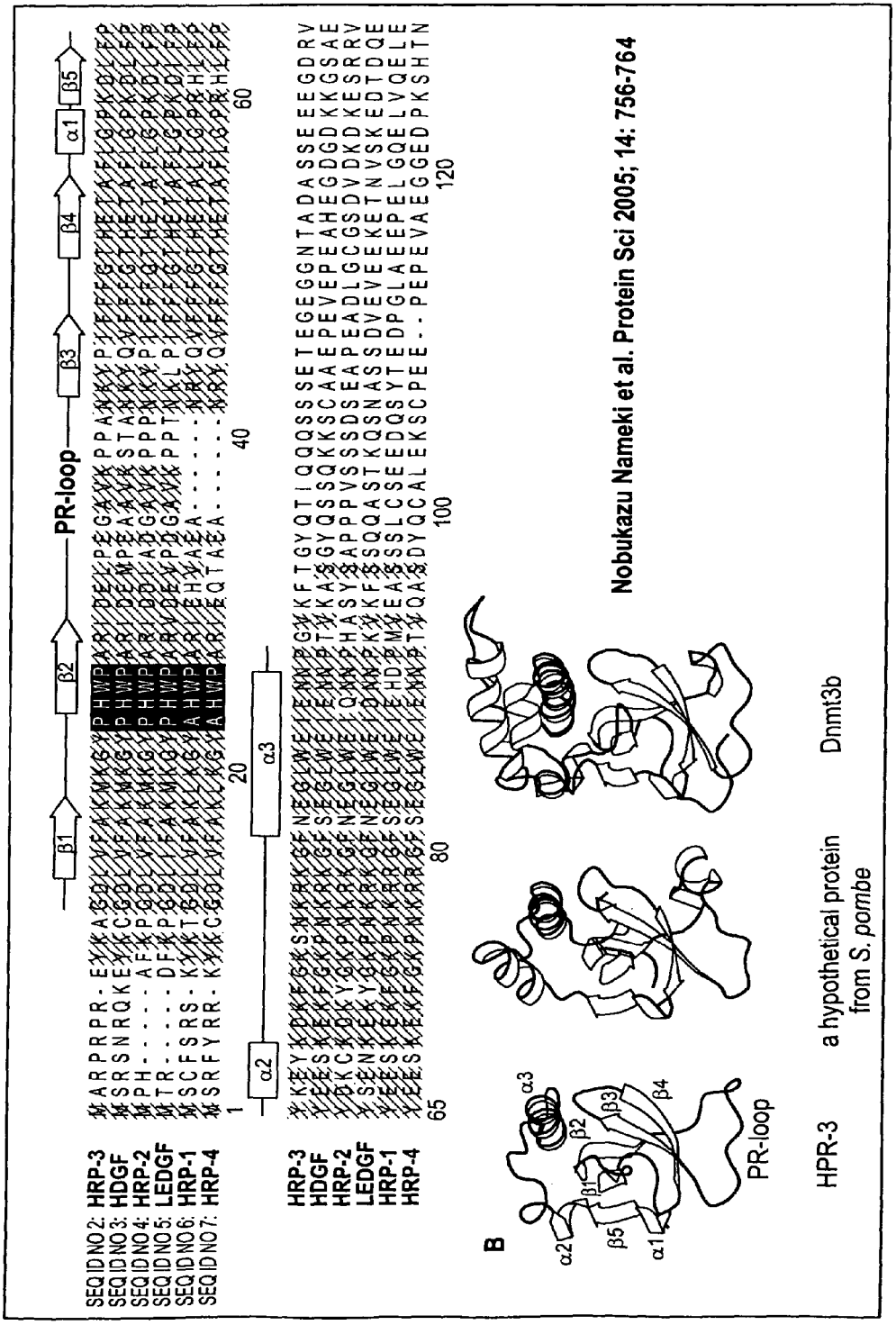
FIG. 1 shows the alignment of the 6 portions of the HDGF family and the structural conservation of the PWWP domain, which is always located to the N-terminus of all the family members.
Figure 2:
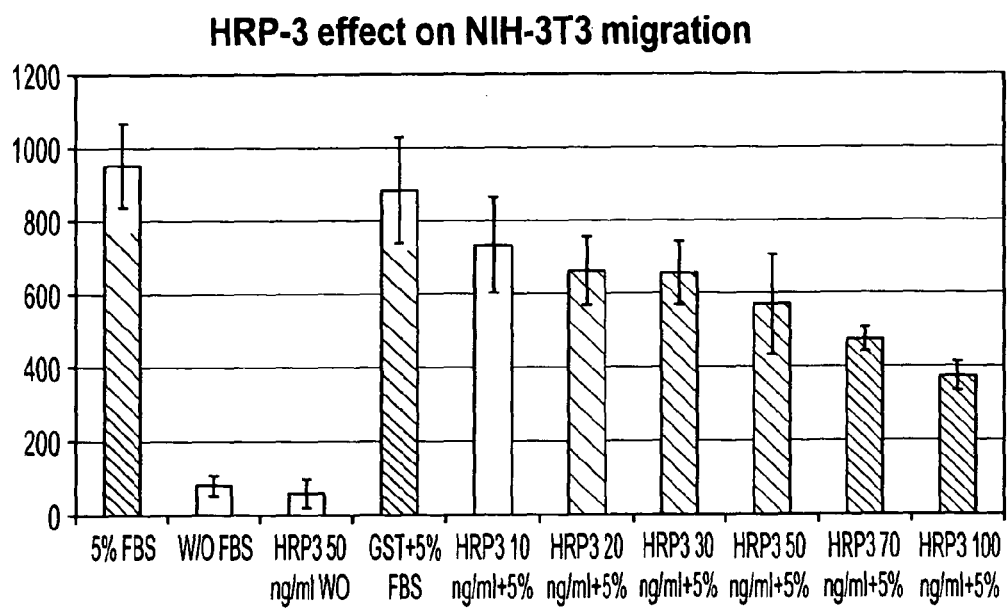
FIG. 2 shows the inhibition effect on NIH-3T3 migration by HRP-3.

In analogy with the reported HDGF activity on NIH 3T3 fibroblast, we decided to test the HRP-3 activity on these cells to develop a test able to report any interfering activity by a ligand able to bind the PWWP domain. Migration and proliferation assay of 3T3 cells in presence of increasing amounts of the protein were performed. These assays allow the definition of a strong anti-migratory effect of the HRP-3 protein, which at 30 ng/mL is able to prevent 50% of the 3T3 migration induced at 24 h by 5% FBS. This test was validated and is currently well reproducible, FIG. 2.

Moreover, it was found that HRP-3 blocks 3T3 proliferation and anchorage independent growth at 0.1 ng/mL. All these data point to an effect of HRP-3 opposite to that of the HDGF, which induces a strong proliferation and migration of 3T3 cells.

Example 2

HRP-3 as Angiogenic Agent for HUVEC Cells

Figure 3:
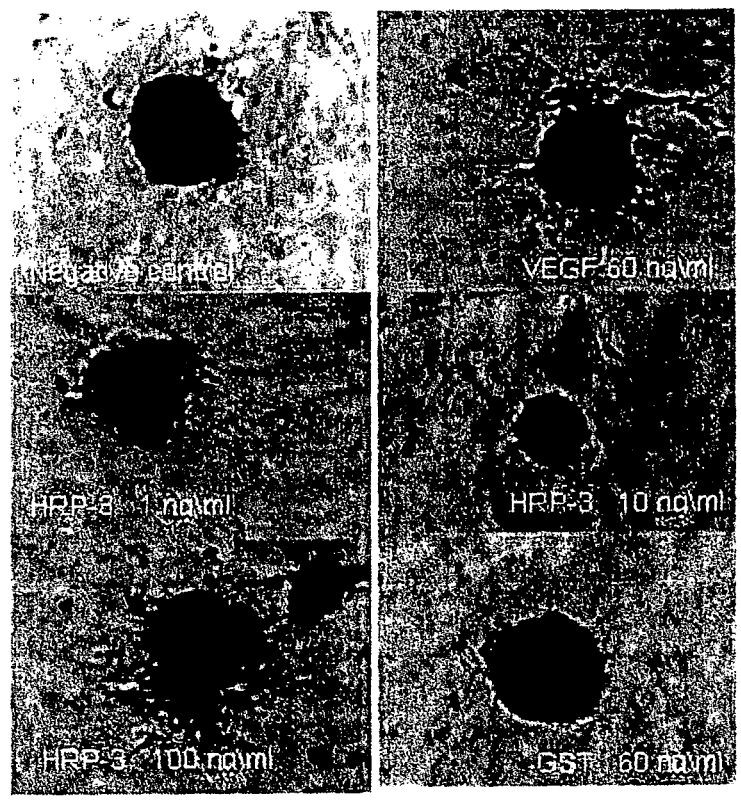
FIGS. 3 and 4 show the dose-dependent HUVEC sprouting induced by HRP-3 after 24 hours of stimulation.
Figure 4:
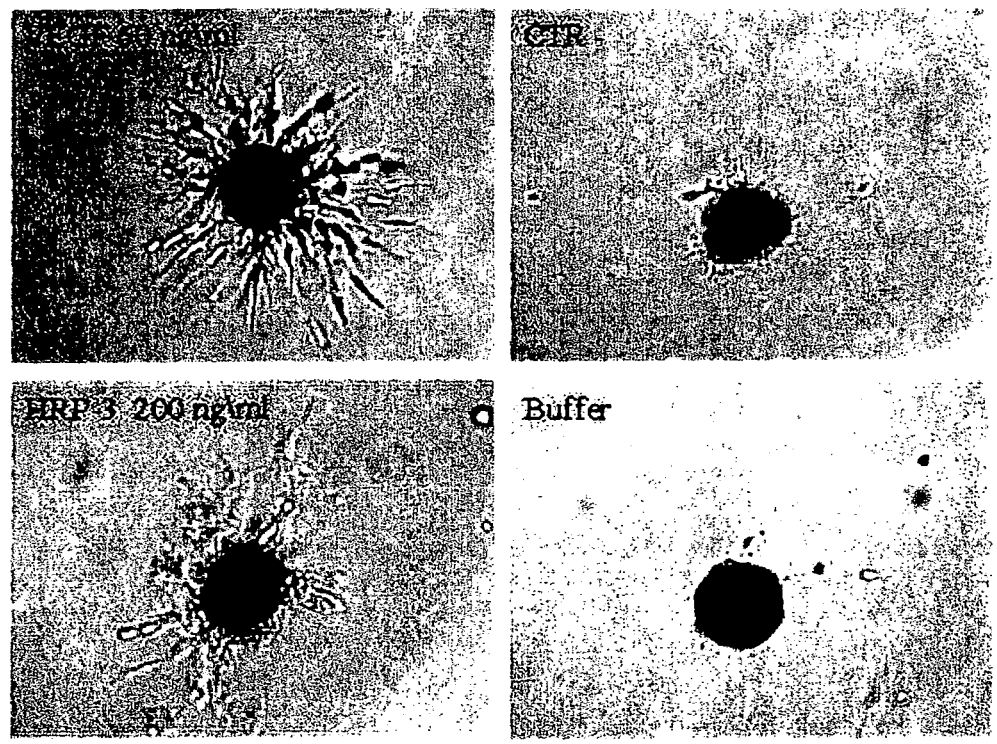

It was found that HDGF is involved in angiogenesis in different kind of tumors for this reason we tested the activity of HRP-3 on endothelial primary cell lines as BAEC and HUVEC. While no effects on the proliferation on BAEC and HUVEC cells were found, HRP-3 is able to induce HUVEC sprouting after 24 hours of stimulation. As shown in FIGS. 3 and 4 the HRP-3 can induce sprouting in HUVEC cells in a dose dependent manner. In FIG. 4 we have shown the negative control and the positive control with VEGF at 60 ng/ml. From this data we demonstrated that HRP-3 stimulate sprouting on HUVEC cells at concentration above 100 ng/ml. To be sure of ours results, experiments have been made in blind too.

Another important aspect of endothelial cells functionality is the ability to form new blood vessels so we performed a tube formation assay in Matrigel; a preliminary result says that HRP-3 is able to maintain vessel-like network of HUVEC after 24 hours, (not shown).

Figure 5:
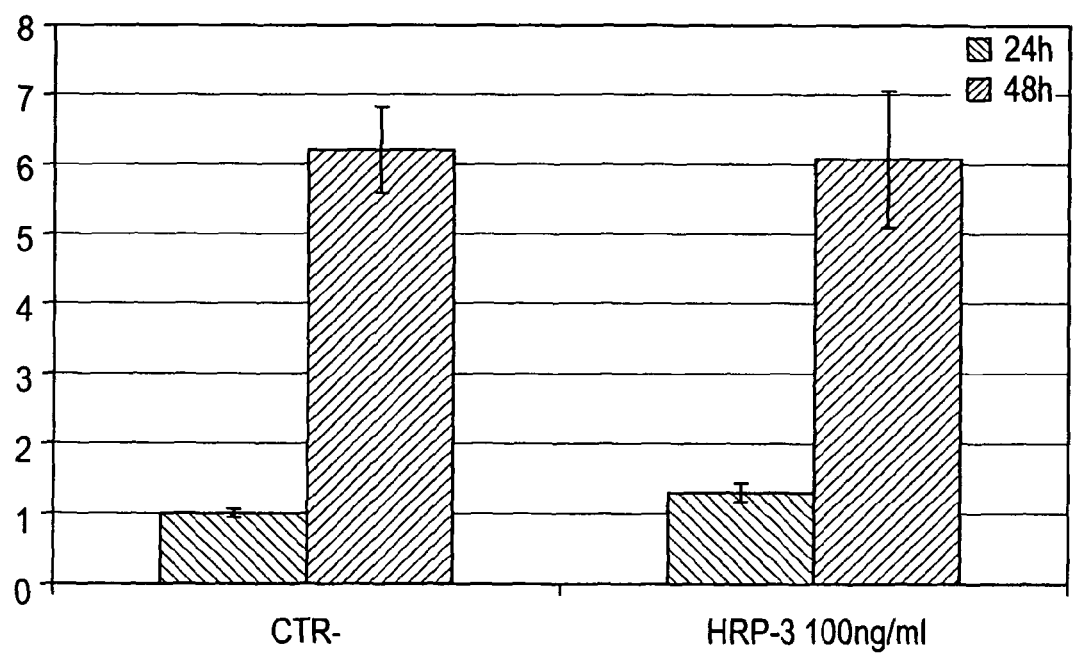
FIGS. 5 and 6 show respectively the VEGFR-2 mRNA expression and the VEGF mRNA expression with and without HRP-3 stimuli in HUVEC cell lines.
Figure 6:
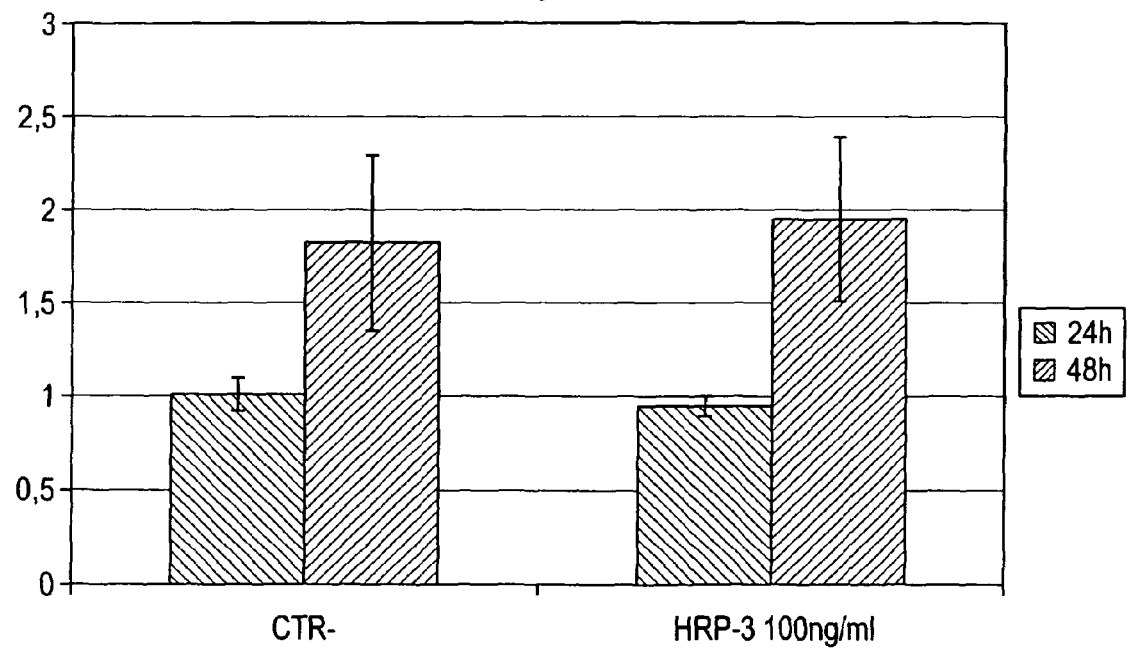

To understand the molecular basis of this stimulation, we studied mRNA expression of HRP-3 in HUVEC cell line by Real Time PCR. Interestingly, the protein was found to be expressed at high levels. To understand if VEGF or VEGFR-2 was involved with the HRP-3 induced mechanism, we stimulated HUVEC cells with our HRP-3 and investigated mRNA levels of VEGF, VEGFR-2, HRP-3 and HDGF. The expression of those genes is not changed by HRP-3, FIGS. 5 and 6.

Figure 7:
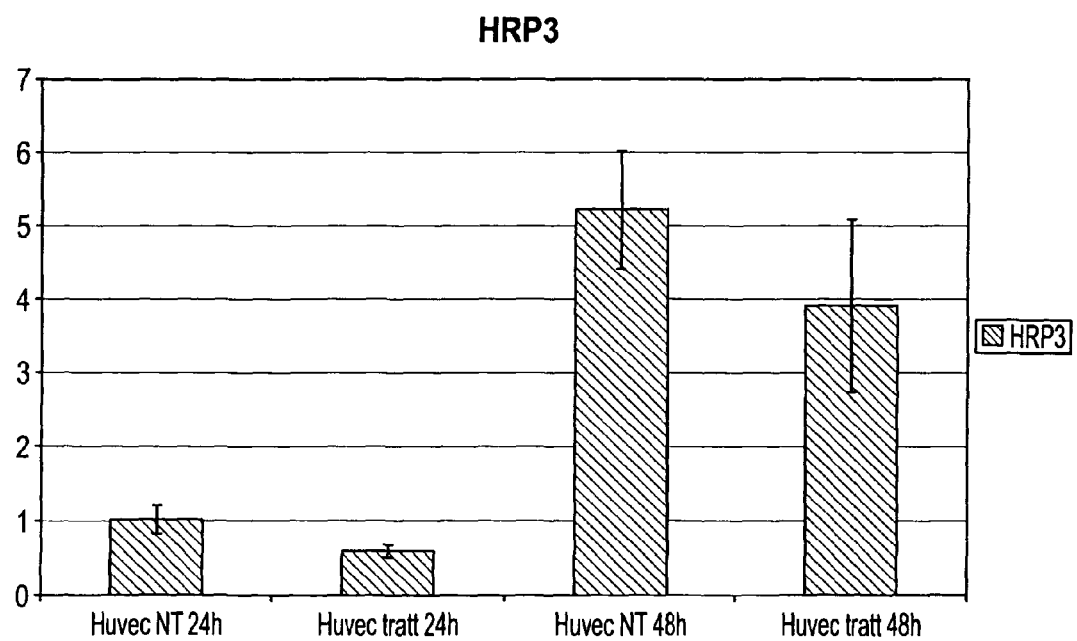
FIG. 7 shows the HRP-3 mRNA expression with and without VEGF stimuli in HUVEC cell lines.

To understand if HRP-3 is controlled on the top by VEGF, we treated HUVEC cells with 60 ng/ml VEGF and than we measured HRP-3 mRNA levels: there was no significant difference between negative control and treated cells (FIG. 7).

From this last data we can accept that the HRP-3 pro-angiogenic activity is VEGF independent.

This proof is very important to block angiogenesis for therapeutical uses.

Figure 8:
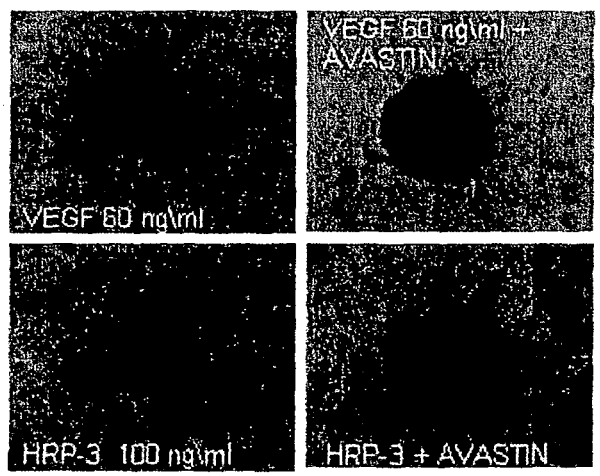
FIG. 8 shows the sprouting test of HUVEC cells with the anti-VEGF antibody Avastin and the HRP-3.

Furthermore to confirm VEGF-independent angiogenic activity we performed another sprouting test with Avastin, anti-VEGF antibody in presence of VEGF and our protein. Avastin is able to blocks HUVEC sprouting VEGF-mediated but not that HRP-3-mediated FIG. 8.

Figure 9:
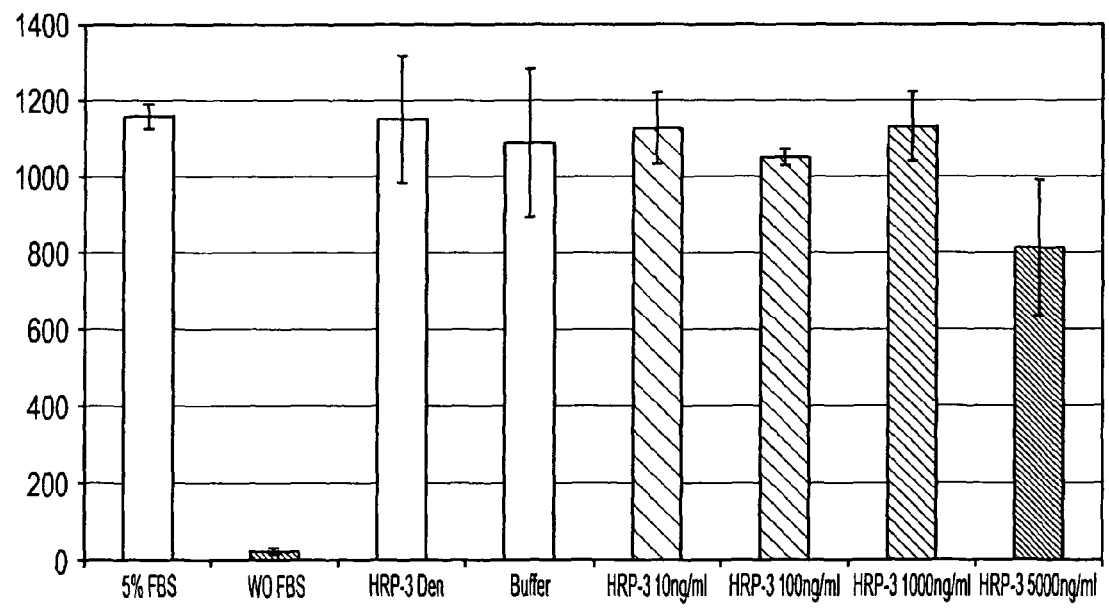
FIG. 9 shows the HUVEC cell migration assay in presence of increasing amounts of HRP-3 protein.

Migration assay of HUVEC in presence of increasing amounts of the protein was performed (FIG. 9). These assay allows the definition of a anti-migratory effect of the protein on human endothelial cells in a dose-dependent manner, which at 100 ng/ml is able to prevent about 80% of the migration induced at 5 and 16 h by 5% FBS.

Example 3

HRP-3 Expression Level in Neural Tumours

From previous publication we know that HDGF expression is increased in different human cancers as melanomas, colorectal, pancreatic, gastric, hepatocellular and lung carcinomas. Thus has been decided to screen for specific overexpression of HDGF protein in human tumour cell line by Real Time PCR and we noticed that the basal mRNA level is higher than HRP-3 on every cell line and up to now HDGF has been found to be overexpressed in breast cancer, neuroblastoma, osteosarcoma, lymphomas, pancreatic and ovarian adenocarcinoma but the biggest overexpression was found in the Chang cell line that are human liver cells.

Figure 10:
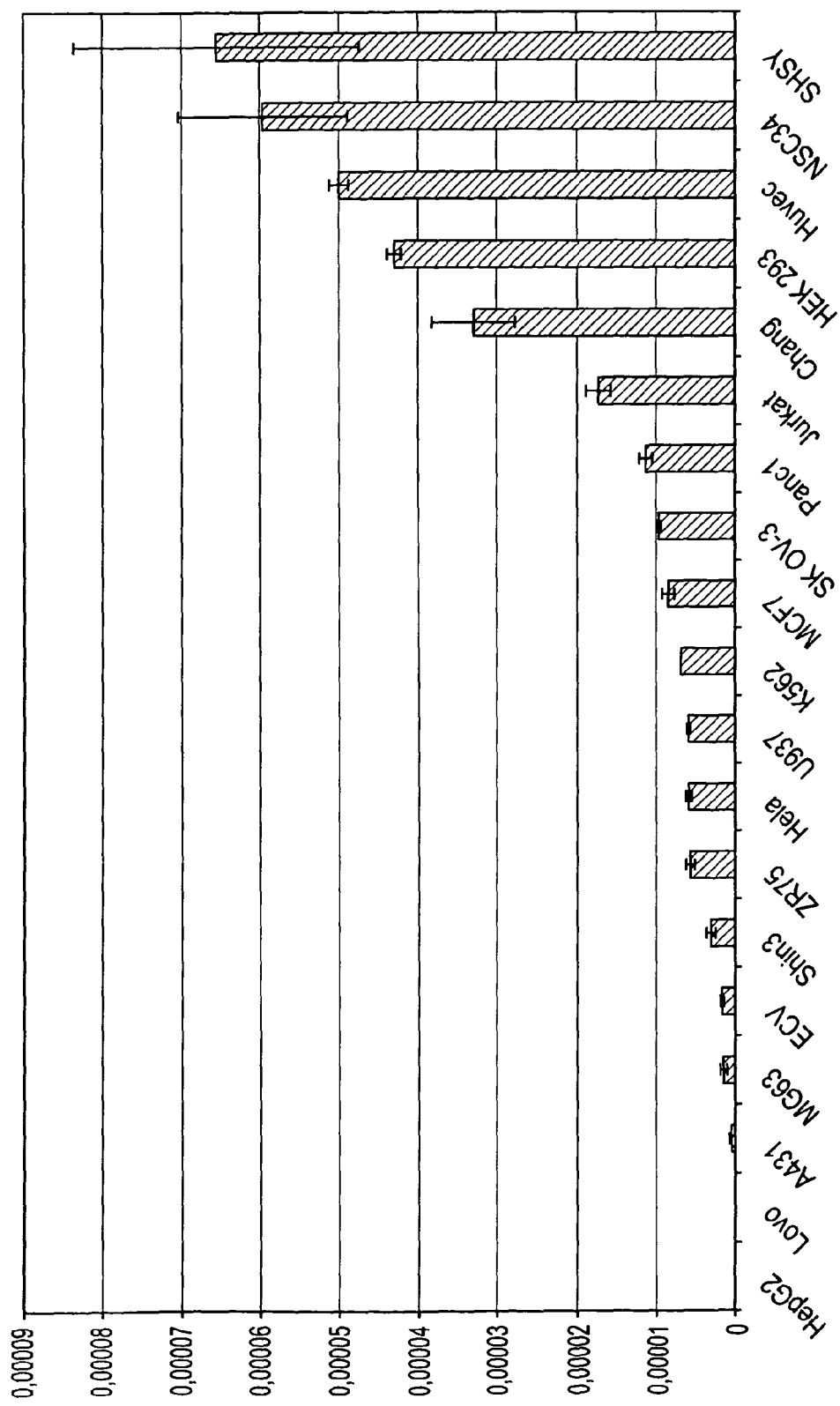
FIG. 10 shows the HRP-3 expression level in different normal and tumoral human cell lines. RNA was extracted from the cells, subjected to DNAse treatment, retrotranscription and Real-Time PCR analysis. 18S RNA levels were used for sample normalization. It was found that HRP-3 protein is highly and selectively expressed by human neuroblastoma cell lines.

Even though HRP3 is to be intended only as a PWWP containing protein to be used as a model for developing PWWP-binding oligonucleotides, we wondered if there is a known pathology where the protein is over-expressed. A bioinformatic screening of array data gave a specific, high level of expression in human glioma of aggressive grade, a rare lethal tumour of children. This overexpression may be related to the proposed proliferative function of HRP-3, and thus we started a screening for specific overexpression of the protein in CNS tumour cell line by Real Time PCR. Interestingly, the protein was found to be overexpressed in SH-SY5 neuroblastoma cells and in NSC34, subclone of a mouse-mouse neural hybrid cell line produced through fusion of the aminopterin-sensitive neuroblastoma N18TG2 with motor neuron-enriched embryonic day 12-14 spinal cord cells (FIG. 10).

The level of expression was specific, since other brain tumour lines, like the neuroblastoma Neuro2A cell line, or cells derived from other tissues, did not express the protein at high levels. The SH-SY5 cells derived from secondary metastasis of an aggressive neuroblastoma, colonizing the bone marrow of a 4 year child. Neuroblastoma is an orphan disease (orphaned ref. ORPHA635), whose in vitro model is currently represented by the SH-SY cells.

Recent findings have suggested that the molecular pathways driving the development of normal neuroectodermal-derived tissues might also be involved in neuroblastoma maturation. Angiogenesis plays a key role during neural differentiation, exerting a trophic activity on both neurons and glia. A variety of angiogenic factors have been identified so far to play an important role in the induction of angiogenesis in NBs, including vascular endothelial growth factor (VEGF). Proliferation assay of SH-SY5 and NCS-34 cells in presence of increasing amounts of the protein were performed. These assays allow the definition of a anti-proliferatory effect of the protein only on SHSY, which at 100 ng/mL is able to prevent 25% of the SH-SY5 proliferation induced at 24 and 48 h by 5% FBS.

Figure 11:
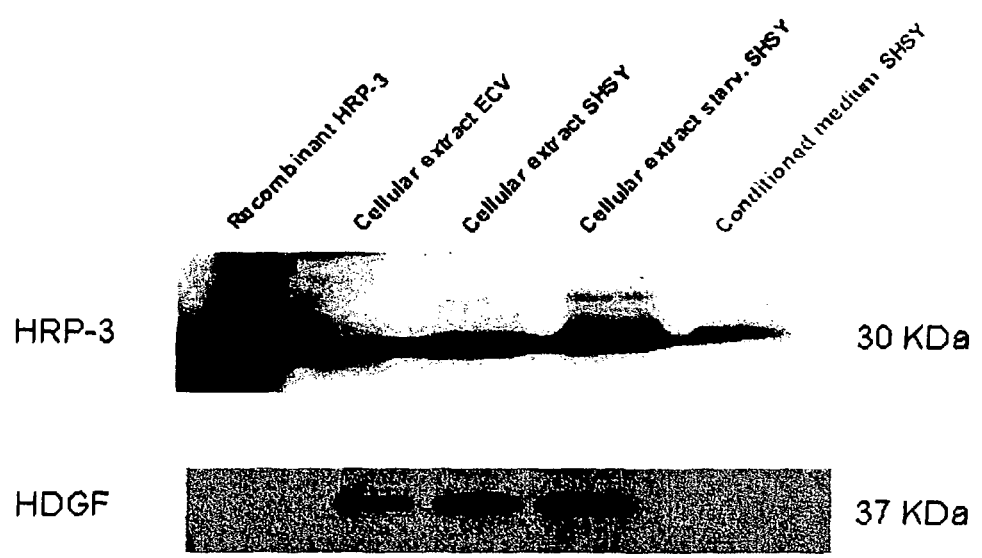
FIG. 11 shows a Western blot assay, whereby HRP-3 protein was found in SHSY conditioned medium.

Inside neuroblastoma we suppose that neuroblastoma cells produce soluble HRP-3 that is able to help new angiogenesis processes in endothelial cells. A result in support of this theory, we find HRP3 protein in SHSY conditioned medium by western blot assay, FIG. 11. This confirms that both HDGF and HRP-3 are highly expressed in SHSY cell but only HRP-3 is present in the medium.

Figure 14A:
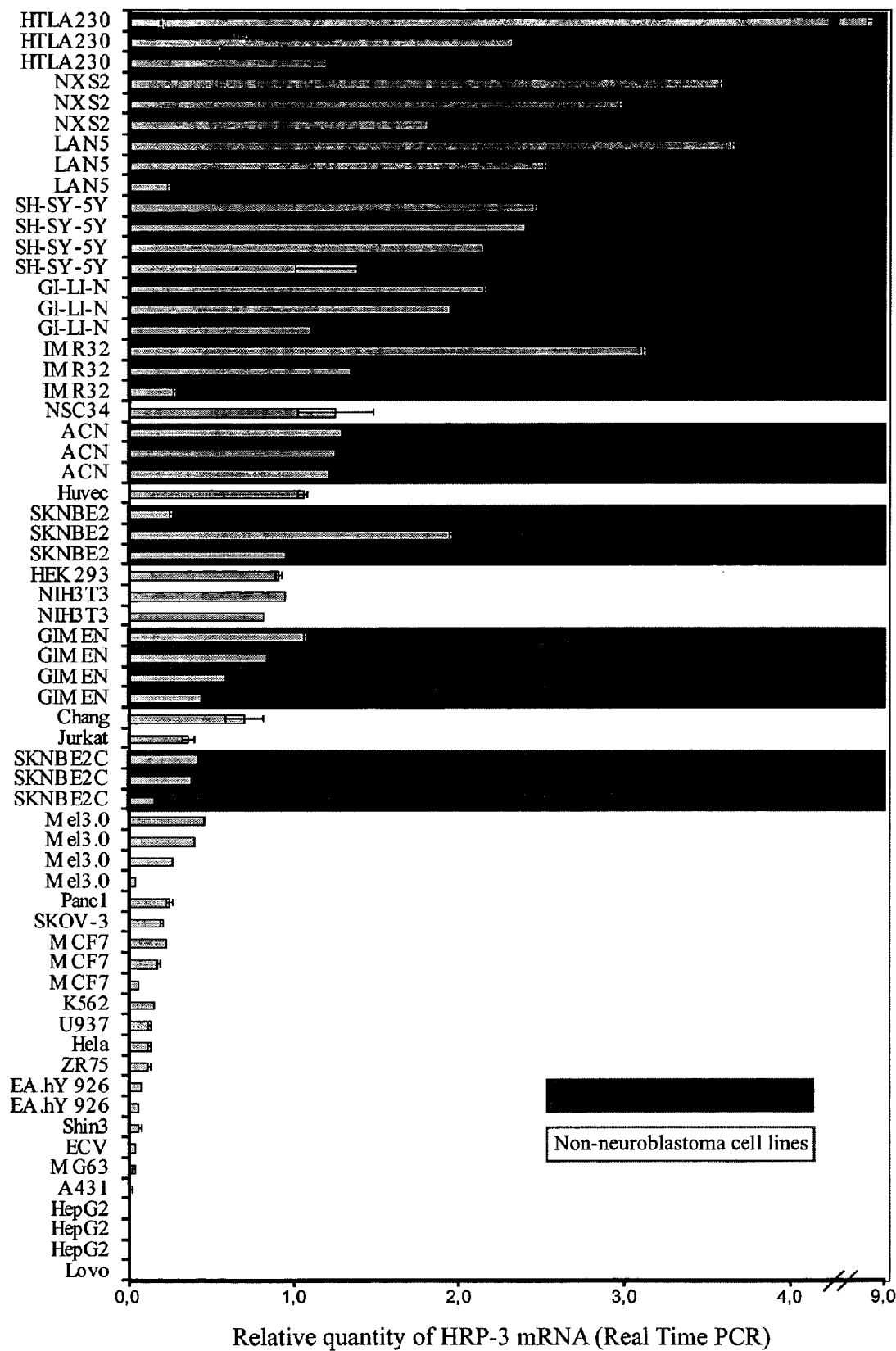
FIG. 14-A) shows HRP-3 transcript levels of neuroblastoma and non-neuroblastoma cell lines. RNA was extracted from the cells, subjected to DNAse treatment, retrotranscription and Real-Time PCR analysis. 18S RNA levels were used for sample normalization. Cell lines were ordered top-down according to mean expression values. Neuroblastoma cell lines are marked in grey.

To further support our theory, we have chosen different neuroblastoma cell lines and analysed the HRP-3 mRNA and protein expression levels. As shown in FIG. 14A, it was found that HRP-3 protein is present at higher levels in neuroblastoma cell lines compared to the other tumor and normal cell lines examined.

Figure 14:
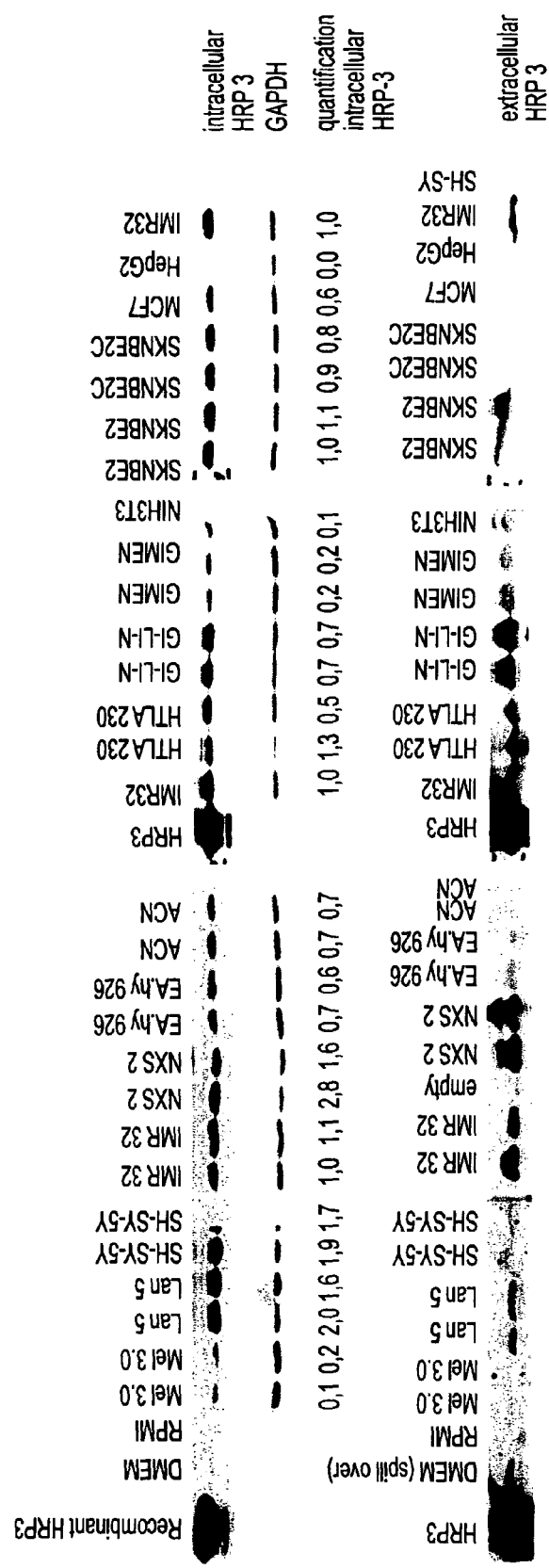

As a next step, we have analyzed whether HRP-3 is released by neuroblastoma cells into the extracellular compartment. The conditioned medium of ten neuroblastoma cell lines was concentrated, proteins were precipitated and analyzed for the presence of HRP-3 by Western Blot analysis. As shown in FIG. 14-B, most neuroblastoma cell lines, including GI-LI-N, NXS2, IMR32, HTLA230, LAN5 and SKNBE2 cells, secrete HRP-3 into their culture media.

Furthermore, we have analyzed HRP-3 expression in tumor tissue derived from two previously described mouse models of neuroblastoma, an orthotopic xenograft model and a pseudometastatic xenograft model (Pastorino et al., 2003; Marimpietri et al., 2007). While the orthotopic injection of GI-LI-N cells into the adrenal gland led to local tumor development, the intravenous injection of HTLA230 cells in the pseudometastatic model led to metastasis development in the kidney. Levels of HRP-3 protein in both tumors were analyzed by Western Blot analysis and compared to HRP-3 expression in kidney and adrenal gland of untreated healthy mice. As shown in FIG. 14-C, HRP-3 was found to be expressed in adrenal and brain tissues, while kidney and liver tissues contained very low levels of HRP-3. Importantly, HRP-3 protein levels in HTLA230 and GI-LI-N tumor tissues exceeded the level in the respective hosting tissues.

Therefore, it can be concluded that HRP-3 expression and secretion by neuroblastoma tissue leads to abnormally high HRP-3 levels in the extracellular tumor environment.

Example 4

HRP-3 Targeting by Oligonucleotides

On the basis of the available structure of the PWWP domain in complex with a duplex DNA, we designed a short (15 bp) duplex DNA and 3 derived DNA double strands to target HRP3 (FIG. 12). The sequences of the designed DNA are shown in the figure on the left, with the red and underlined bases highlighting the changes introduced with the duplex of Lukasik et al (Duplex 1). This duplexes have been designed to test different molecular shapes (Duplex 3) and understand how is important the sequence for the binding (Duplex 2 and 4).

Figure 13:
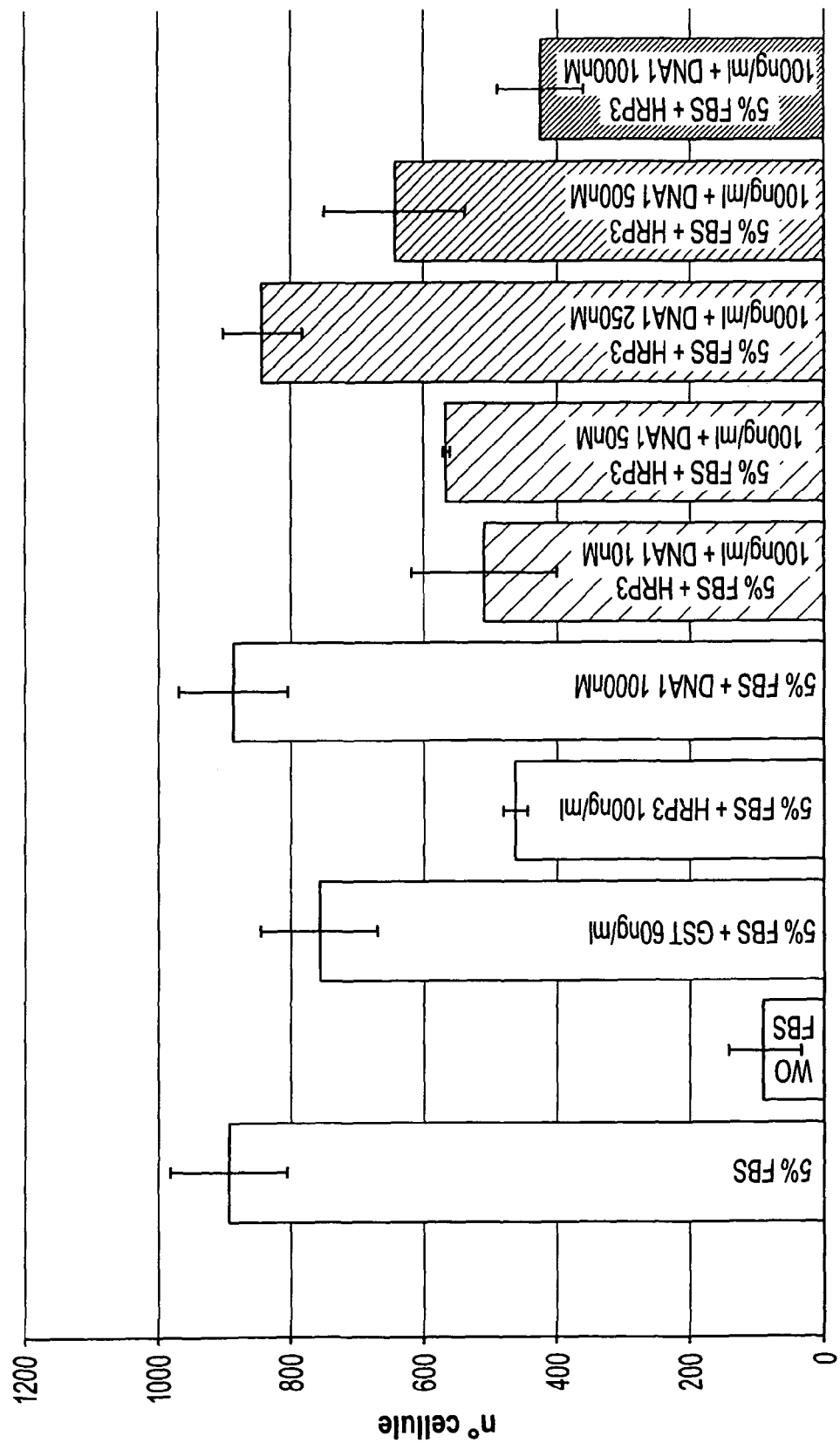
FIG. 13 shows the 3T3 migration in vitro assay with the DNA Duplex 1 (DNA1) of FIG. 12.

All the four DNA duplexes were tested in our 3T3 migration in vitro assay to see if they were able to prevent HRP-3 function by binding its PWWP domain (FIG. 13). In FIG. 13, the first column from the left shows the migration of the control with FBS and the second column from the left the migration of the control without FBS. The third column on the left is the negative control. The forth column from the left shows the migration inhibition in the presence of HRP-3. The fifth column from the left shows that Duplex 1 (DNA 1) at a concentration of 1000 nM does not have any influence on the migration compared to the control with the FBS. The further data show that DNA 1 inhibits the anti-migratory effect of HRP-3 in a concentration-dependent manner. In particular, at a concentration of 250 nM of DNA 1 the migration of 3T3 cells is comparable with the control with FBS. Hence, the Duplex 1 is able to abolish the protein effect of HRP-3. This effect is dose dependent, and is specifically related to the structure, since a single strand does not show any activity.

We found only a modest activity of Duplex 2, and no activity for Duplex 3 and 4. These last data are particularly interesting, since they confirm that the binding is due mainly at a structure-specific activity of the oligos.

Moreover, since it is active on HUVEC cells, we performed a migration assay where Duplex 1 at 50 nM concentration is able to restore totally anti-migratory activity of HRP-3 (data not shown).

Figure 19:
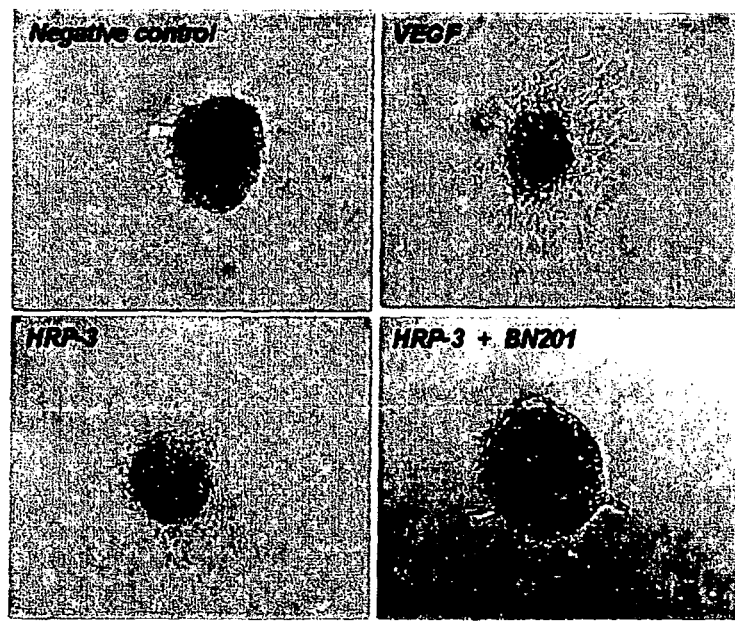
FIG. 19 shows that the oligonucleotide of SEQ ID NO. 16 can block HRP-3 induced sprouting of HUVEC.

We tried to twice block the protein effect of human endothelial cells sprouting with a modified single strand oligonucleotides. In samples with recombinant protein, and synthetic oligos, SEQ ID NO. 16, 17, and 18 the number of sprouted spheroids was reduced as compared to samples with recombinant protein (FIG. 19).

Starting from this result we have obtained oligonucleotide sequences with a hairpin structure according to the present invention with improved resistance in mouse serum (FIG. 15). By introducing chemical modifications, e.g. 2'-OMe, 2'F or inversed polarity, we have designed molecules sequences according to the invention with a better pharmacokinetic profile. These sequences may preferably be conjugated with linear and branched PEG.

In the following sequences according to the invention, the monomers that are underlined and in bold or starred are modified nucleotide building blocks: the underlined and bolded monomers are synthetic 2'-OMe RNA building blocks, and the starred monomers are nucleotide building blocks with a terminal group NH2 in 5' (5'Amino group) which can form an amide bond with the PEG unit. The monomer "iA" refers to an inversed polarity, i.e. to a building block with an 3'-3' inverted linkage.

Sequences

```
SEQ. ID 16)
5'-TAC AAC ACC CAC AAA AAA TTT GTG GGT GTT GTA-3'

SEQ. ID 17)
5'-UAC AAC ACC CAC AAA AAA UUU GUG GGU GUU GUA-3'
(2'-OMe)

SEQ. ID 18)
5'-TAC AAC ACC CAC AAA-[CH_2CH_2O]_5-TTT GTG GGT GTT
GTA-[CH_2CH_2O]_5H-3'
```

-continued

```
SEQ ID 19)
5'-TAC AAC ACC CAC AAA-[CH₂CH₂O]₃-TTT GTG GGT GTT
GTA-[CH₂CH₂O]₃H-3'

SEQ ID 20)
5'-UAC AAC ACC CAC AAA AAA TTT GTG GGT GTT GUA-3'

SEQ ID 21)
5'-UAC AAC ACC CAC AAA AAA TTT GTG GGT GTT GUA-3'

SEQ ID 22)
5'-UAC AAC ACC CAC AAA AAA UTT GTG GGT GTT GUA-3'

SEQ ID 23)
5'-(NH)-T*AC AAC ACC CAC AAA AAA UTT GTG GGT GTT
GTA-'

SEQ ID 24)
5'PEG-(NH)-T*AC AAC ACC CAC AAA AAA UTT GTG GGT
GTT GTA-3'

SEQ ID 25)
5'-(NH)-T*AC AAC ACC CAC AAA AAA UTT GTG GGT GTT
GTiA-3'

SEQ ID 26)
5'-PEG (40 KDa)-(NH)-T*AC AAC ACC CAC AAA AAA UTT
GTG GGT GTT GTiA-3'
```

Example 5

Cytotoxicity Tests

Figure 16B:
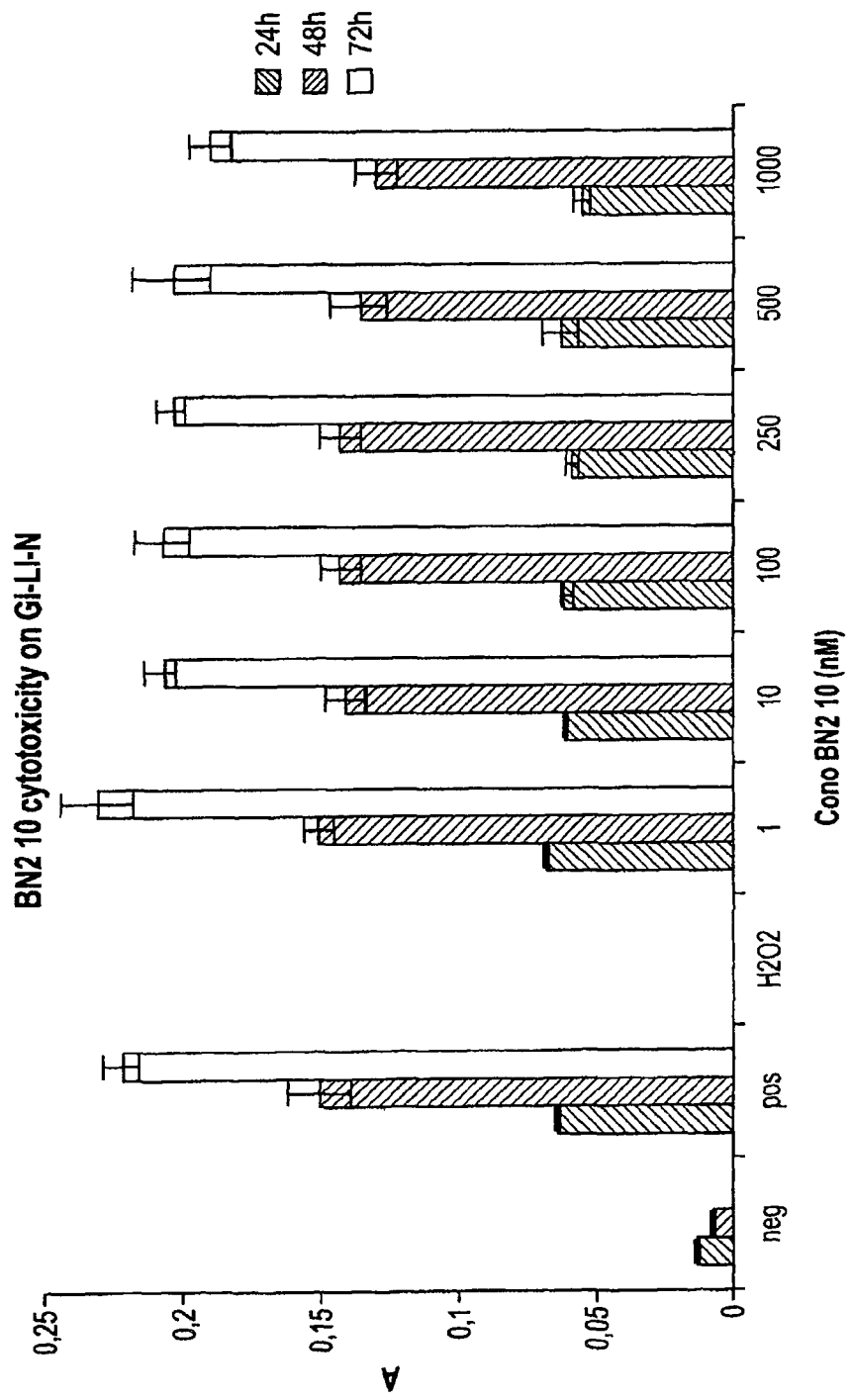
Figure 17:
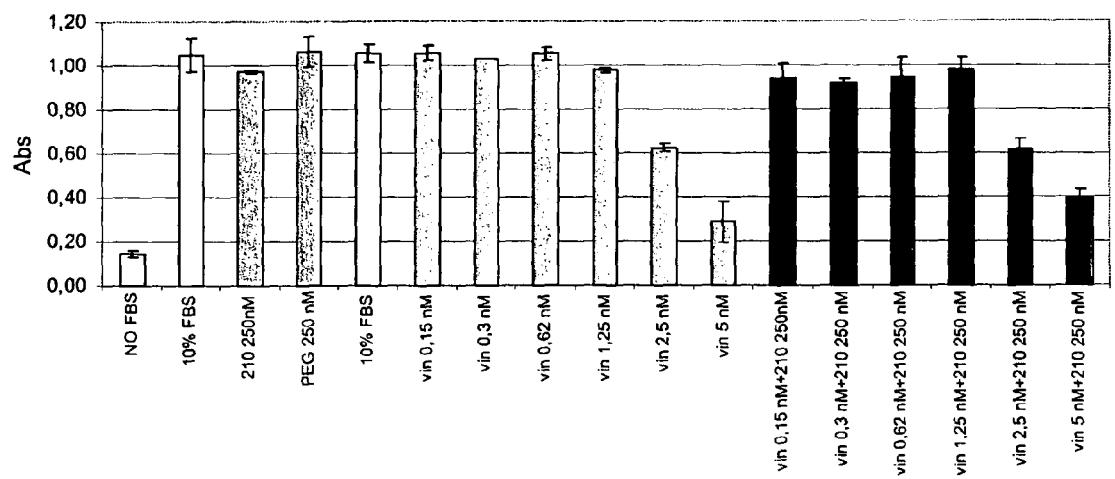
FIG. 17 shows the in vitro cytoxicity of vinicristine (VIN) alone or in combination with the oligonucleotide molecule of sequence SEQ ID NO. 26 (BN210). GI-L-IN neuroblastoma cells were treated with vincristine at concentrations ranging from 0.15 to 5 nM, used alone or in combination with 250 nM BN210. After 48 h, MTT test was performed.

Starting from the ability of these sequences to bind (ref. Lukasik et al., 2006) and block (data not shown) in vitro the pro-angiogenetic effect of soluble HRP-3, we have decided to test the cytotoxicity of SEQ ID NO. 26 (identified with the compound name BN210) in different cell lines, as shown in FIG. 16, and its acute toxicity in vivo.

We have evaluated in vivo the acute toxicity of BN210. 30 CD-1 female mice (Charles River Italia s.r.l., Via Indipendenza, 11-23885 CALCO (Lecco)), weighing 21.8-22.9 g, were divided in 6 groups, each of 5 animals, and housed in Makrolon cages (type III) at a room temperature of 22±3° C. and at a relative humidity of 55±15%. Air changes were 180-220/hour. Three doses of BN210, dissolved in phosphate buffered saline, were tested: 3, 10 and 30 mg/kg given intravenously (i.v., via the tail vain) or intraperitoneally (i.p.). BN210 concentrations in the formulates were 0.155, 0.517 and 1.551 mg/ml, respectively. Mice were observed daily, twice/day, for the appearance of toxicity signs during the 14 days following drug administration. The parameters commonly checked in the Irvin test were taken into consideration. Throughout the period of observation no signs of clinical or behavioural alterations, at all the three doses administered either i.v. or i.p., were detected. After 14 days of observation, all mice were sacrificed and dissected for gross pathology examination. Any sign or pathological alterations were the subject of close scrutiny during the necropsy. No macroscopic signs or pathological changes were detected during necroscopy examination.

We have further investigated the possibility that BN210 has synergistic effect(s) with vincristine, one of the most potent chemotherapic agents in clinical use. To do this, we have performed a MTT test on GI-L-IN neuroblastoma cells with 250 nM BN210 alone or in combination with different concentrations of vincristine. As shown in FIG. 4, while vincristine was able to inhibit proliferation of GI-LI-N cells at a concentration of 2.5-5 nM, the addition of 250 nM BN210 did not enhance or inhibit the effect of vincristine treatment. Moreover, BN210 alone, or PEG-tail alone, did not show any cytotoxic effects on the GI-LI-N cells.

Example 6

In Vivo Model

In previous experiments, BN210 has been shown to possess an anti-angiogenic activity in vitro (data not shown). Therefore, we tested the efficacy of BN210 in vivo in a model of tumor angiogenesis. Neuroblastoma was chosen as tumor model since HRP-3 is principally expressed in the nervous system in mice, and previous experiments have shown that HRP-3 is present and overexpressed in the conditioned medium of various human neuroblastoma cell lines. Since HRP-3 does not affect proliferation of any of the cell lines tested, it has been found adequate to use BN210 in combination with a cytotoxic agent, vincristine.

Mice were housed under specific pathogen-free conditions. The in vivo experiment was performed using five week old female athymic (Nude-nu) mice. Mice were anaesthetized with a mixture of xylazine (10 mg/kg) and ketamine (90 mg/kg) (Imalgene 1000, Merial Italia S.p.A., Milan, Italy), subjected to laparatomy, and orthotopically injected with the neuroblastoma (NB) cell line, GI-LI-N (1.5×10$^6$ cells in 10 μL of saline solution/mouse), in the capsule of the left adrenal gland, as previously reported (Pastorino F. et al., Cancer Res 63, 2003; Pastorino F. et al., Clin Cancer Res 2008). No mortality was observed following tumour cells implantation. NB tumours were allowed to grow from the injected cells for 22 days, then animals were randomly divided in 3 groups. One group was treated i.v., once a week for 5 weeks, with 1 mg/kg of vincristine (VCR, 5 administration in total). A second group of animals was treated with a combination of VCR (i.v. injection of 1 mg/kg, once a week for 5 weeks, 5 administration in total) and BN210 (i.p. injection of 7 mg/kg, 5 days/week, 20 administrations in total). Negative control mice were treated with HEPES-buffered saline. The significance of the differences between experimental groups (n=8 mice/group) in the survival experiments was determined by Kaplan-Meier curves by the use of Chi square log-rank test. These findings were considered significant if P values were <0.05.

Figure 18:
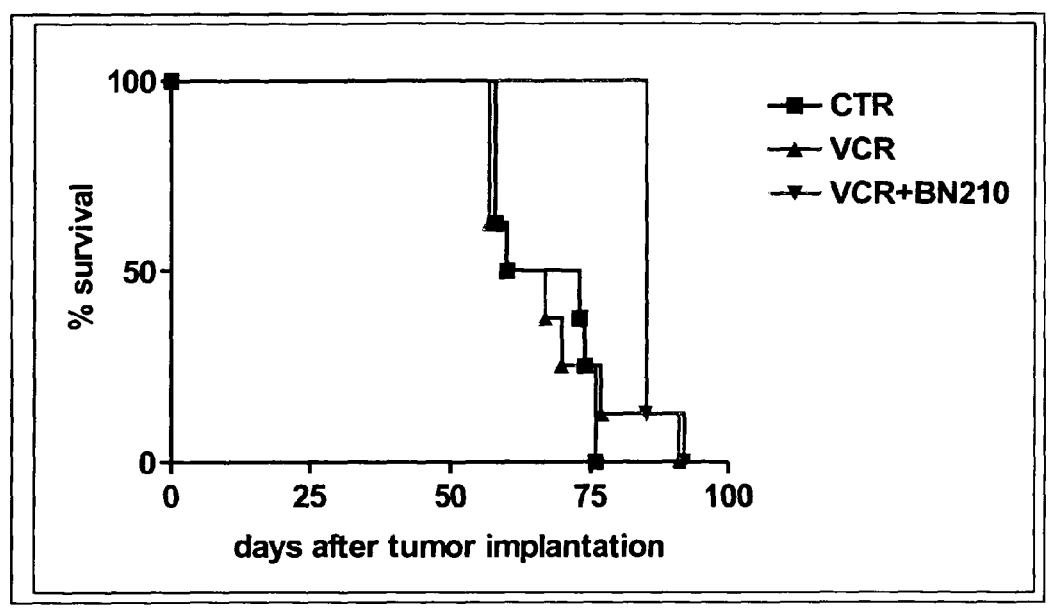
FIG. 18 shows the results of the in vivo activity of the inventive oligonucleotide molecule of sequence SEQ ID NO. 26 (BN210) in combination with the chemotherapeutic agent vincristine (VCR) against thyrotropic neuroblastoma xenografts.

In Vivo Anti-Tumor Activity of Sequence SEQ ID NO. 26 (BN210) in Combination with Vincristine (VCR) Against Orthotopic Neuroblastome (NB) Xenograft To determine whether BN210 could be used to improve the therapeutic effect of VCR in NB xenografts, compared to VCR administered alone, we injected GI-LI-N cells into the left adrenal gland of nude mice and allowed them to grow until they reached a size of approximately 200 mm$^3$ (22 days). NB tumour-bearing mice were then treated at weekly intervals with the drugs, as reported above. As shown in FIG. 18, NB-bearing mice treated with VCR alone (1 mg/kg i.v., a sub-therapeutic dose in this experiment) did not show any increase of their life span compared with negative control mice. On the contrary, mice treated with the combination of VCR plus BN210 had a statistically significant increase of their life span, compared to the negative control and the VCR treatment groups (p=0.0058) (FIG. 18).

The invention claimed is:

1. A single-stranded oligonucleotide molecule comprising the sequence

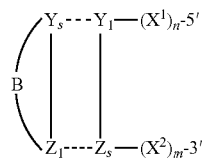

wherein the sequence

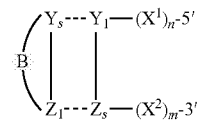

is 5'-$(X^1)_m$-TAC AAC ACC CAC AAA-B-TTT GTG GGT GTT GTA-$(X^2)_m$-3' (SEQ ID NO:1), wherein A, C, T and G represent nucleotide or nucleotide analogue building blocks, $X^1$ and $X^2$ are independently selected from moieties comprising poly(alkylene glycol) units, n and m independently represent 0 or 1, wherein at least one of n and m is 1, and B represents a bridging moiety.

2. The oligonucleotide molecule of claim 1, wherein the nucleotide or nucleotide analogue are selected from deoxyribonucleotide building blocks, modified deoxyribonucleotide building blocks, ribonucleotide building blocks, modified ribonucleotide building blocks, nucleotide analogue building blocks and morpholino building blocks or combinations thereof.

3. The oligonucleotide molecule of claim 1, wherein $X^1$ and $X^2$ are selected from moieties comprising linear or branched poly(ethylene glycol) units having a molecular weight in the range between 200 and 100,000 Da.

4. The oligonucleotide molecule of claim 1, wherein B is a spacer sequence of up to 20 building blocks capable of connecting the complementary nucleotide or nucleotide analogue building blocks and supporting the forming of base pairs.

5. The oligonucleotide molecule of claim 1, wherein B is a binding moiety comprising
  (i) a nucleotidic spacer sequence of at least 3 unpaired nucleotide or nucleotide analogue building blocks, or
  (ii) a non-nucleotidic spacer sequence.

6. The oligonucleotide molecule of claim 1 for inhibiting a PWWP domain protein selected from the group consisting of HDGF, HRP-1, HRP-2, HRP-3, HRP-4 and LEDGF.

7. The oligonucleotide molecule of claim 1, which binds to a PWWP domain protein with an affinity of at least 10 μM.

8. The oligonucleotide molecule, of claim 1 in combination with a pharmaceutically acceptable carrier, diluent and/or adjuvant for diagnostic and/or therapeutic applications.

9. The oligonucleotide molecule of claim 8, wherein said pharmaceutically acceptable carrier, diluent and/or adjuvant is suitable for use in the diagnosis and therapy of conditions or disorders associated with, accompanied by and/or caused by a PWWP domain protein dysfunction.

10. The oligonucleotide of claim 8, wherein said pharmaceutically acceptable carrier, diluent and/or adjuvant is suitable for use in the diagnosis and therapy of angiogenesis-related disorders.

11. The oligonucleotide molecule of claim 8 in combination with further medicaments.

12. The oligonucleotide of claim 1, in combination with a carrier, diluent and/or adjuvant suitable for use in drug screening.

13. The compound of claim 12, wherein said pharmaceutically acceptable carrier, diluent and/or adjuvant is suitable for inhibiting cellular migration, proliferation and/or anchorage independent growth.

14. The HRP-3 antagonist of claim 8, wherein said pharmaceutically acceptable carrier, diluent and/or adjuvant is suitable for use in an agent for inhibiting angiogenesis.

15. The oligonucleotide of claim 10, wherein said pharmaceutically acceptable carrier, diluent and/or adjuvant is suitable, for use in the diagnosis and therapy of cancer selected from the group consisting of neuroblastoma, melanoma, colorectal cancer, pancreatic cancer, gastric cancer, hepatocellular cancer and lung cancer.

16. The oligonucleotide molecule of claim 6, wherein said PWWP domain protein is HRP-3 or HDGF.

17. The oligonucleotide molecule of claim 5, wherein said non-nucleotidic spacer sequence is a poly(ethylene glycol) spacer sequence of at least 5 ethylene glycol units.

18. The oligonucleotide molecule of claim 2, wherein the nucleotide analogue building blocks are selected from the group consisting of PNA, LNA, and O-Methyl RNA.

19. The oligonucleotide molecule according to claim 1 wherein s is an integer between 5 and 18.

20. The oligonucleotide molecule of claim 7, which binds to a PWWP domain protein with an affinity of at least 100 µM.

21. The oligonucleotide molecule of claim 20, which binds to a PWWP domain protein with an affinity of at least 1000 µM.

22. A method for diagnosing or treating conditions or disorders associated with, accompanied by and/or caused by a PWWP domain protein dysfunction, comprising administering a single-stranded oligonucleotide molecule for a PWWP domain protein, to a patient in need of such diagnosis or treatment, wherein said single-stranded oligonucleotide molecule comprises the sequence 5'-$(X^1)_m$-TAC AAC ACC CAC AAA-B-TTT GTG GGT GTT GTA-$(X^2)_m$-3' (SEQ ID NO:1), wherein A, C, T and G represent nucleotide or nucleotide, analogue building blocks, $X^1$ and $X^2$ are independently selected from moieties comprising poly(alkylene glycol) units, n and m independently represent 0 or 1, wherein at least one of n and m is 1, and B represents a bridging moiety.

23. The method according to claim 22, wherein said patient is suspected of suffering from an angiogenesis-related disorder.

24. The method according to claim 23, wherein said angiogenesis-related disorder is selected from the group consisting of neuroblastoma, melanoma, colorectal cancer, pancreatic cancer, gastric cancer, hepatocellular cancer and lung cancer.

25. The method according to claim 22, further comprising treating said patient with irradiation, surgery and/or administration of further medicaments.

26. A method for screening for molecules which modulate the interaction of PWWP domain protein oligonucleotide molecules and their target proteins, comprising combining a molecule to be tested with a single-stranded oligonucleotide molecule comprising the sequence 5'-$(X^1)_m$-TAC AAC ACC CAC AAA-B-TTT GTG GGT GTT GTA-$(X^2)_m$-3' (SEQ ID NO:1), wherein A, C, T and G represent nucleotide or nucleotide analogue building blocks, $X^1$ and $X^2$ are independently selected from moieties comprising poly(alkylene glycol) units, n and m independently represent 0 or 1, wherein at least one of n and m is 1, and B represents a bridging moiety, and a target protein, and determining whether the molecule to be tested modulates the interaction of the PWWP domain protein oligonucleotide molecule and the target protein.

\* \* \* \* \*

SEQUENCE LISTING

<160> NUMBER OF SEQ ID NOS: 26

<210> SEQ ID NO 1
<211> LENGTH: 33
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: k is equal to 5'-X1n where, in conjunction with
      (d), X1 and X2 are independently selected from moieties comprising
      poly(alkylene glycol) units, n and m independently represent 0 or
      1, wherein at least one of n and m is 1
<220> FEATURE:
<221> NAME/KEY: misc_feature2
<222> LOCATION: (15)..(16)
<223> OTHER INFORMATION: B represents a bridging moiety
<220> FEATURE:
<221> NAME/KEY: misc_feature3
<222> LOCATION: (30)..(30)
<223> OTHER INFORMATION: d is equal to 3'-X2m where, in conjunction with
      (k), X1 and X2 are independently selected from moieties comprising
      poly(alkylene glycol) units, n and m independently represent 0 or
      1, wherein at least one of n and m is 1

<400> SEQUENCE: 1
ktacaacacc cacaaabttt gtgggtgttg tad                               33

<210> SEQ ID NO 2
<211> LENGTH: 129
<212> TYPE: PRT
<213> ORGANISM: Mus musculus

<400> SEQUENCE: 2

Met Ala Arg Pro Arg Pro Arg Glu Tyr Lys Ala Gly Asp Leu Val Phe
1               5                   10                  15

Ala Lys Met Lys Gly Tyr Pro His Trp Pro Ala Arg Ile Asp Glu Leu
            20                  25                  30

Pro Glu Gly Ala Val Lys Pro Pro Ala Asn Lys Tyr Pro Ile Phe Phe
        35                  40                  45

Phe Gly Thr His Glu Thr Ala Phe Leu Gly Pro Lys Asp Leu Phe Pro
    50                  55                  60

Tyr Lys Glu Tyr Lys Asp Lys Phe Gly Lys Ser Asn Lys Arg Lys Gly
65                  70                  75                  80

Phe Asn Glu Gly Leu Trp Glu Ile Glu Asn Asn Pro Gly Val Lys Phe
                85                  90                  95

Thr Gly Tyr Gln Thr Ile Gln Gln Gln Ser Ser Ser Glu Thr Glu Gly
            100                 105                 110

Glu Gly Gly Asn Thr Ala Asp Ala Ser Ser Glu Glu Glu Gly Asp Arg
        115                 120                 125

Val

<210> SEQ ID NO 3
<211> LENGTH: 130
<212> TYPE: PRT
<213> ORGANISM: Mus musculus

<400> SEQUENCE: 3

Met Ser Arg Ser Asn Arg Gln Lys Glu Tyr Lys Cys Gly Asp Leu Val
1               5                   10                  15

Phe Ala Lys Met Lys Gly Tyr Pro His Trp Pro Ala Arg Ile Asp Glu

```
              20                  25                  30
Met Pro Glu Ala Ala Val Lys Ser Thr Ala Asn Lys Tyr Gln Val Phe
            35                  40                  45

Phe Phe Gly Thr His Glu Thr Ala Phe Leu Gly Pro Lys Asp Leu Phe
        50                  55                  60

Pro Tyr Glu Glu Ser Lys Glu Lys Phe Gly Lys Pro Asn Lys Arg Lys
65                  70                  75                  80

Gly Phe Ser Glu Gly Leu Trp Glu Ile Glu Asn Asn Pro Thr Val Lys
                85                  90                  95

Ala Ser Gly Tyr Gln Ser Ser Gln Lys Lys Ser Cys Ala Ala Glu Pro
            100                 105                 110

Glu Val Glu Pro Glu Ala His Glu Gly Asp Gly Asp Lys Lys Gly Ser
        115                 120                 125

Ala Glu
    130

<210> SEQ ID NO 4
<211> LENGTH: 125
<212> TYPE: PRT
<213> ORGANISM: Mus musculus

<400> SEQUENCE: 4

Met Pro His Ala Phe Lys Pro Gly Asp Leu Val Phe Ala Lys Met Lys
1               5                   10                  15

Gly Tyr Pro His Trp Pro Ala Arg Ile Asp Asp Ile Ala Asp Gly Ala
            20                  25                  30

Val Lys Pro Pro Pro Asn Lys Tyr Pro Ile Phe Phe Phe Gly Thr His
        35                  40                  45

Glu Thr Ala Phe Leu Gly Pro Lys Asp Leu Phe Pro Tyr Asp Lys Cys
    50                  55                  60

Lys Asp Lys Tyr Gly Lys Pro Asn Lys Arg Lys Gly Phe Asn Glu Gly
65                  70                  75                  80

Leu Trp Glu Ile Gln Asn Asn Pro His Ala Ser Tyr Ser Ala Pro Pro
                85                  90                  95

Pro Val Ser Ser Ser Asp Ser Glu Ala Pro Glu Ala Asp Leu Gly Cys
            100                 105                 110

Gly Ser Asp Val Asp Lys Asp Lys Glu Ser Arg Arg Val
        115                 120                 125

<210> SEQ ID NO 5
<211> LENGTH: 125
<212> TYPE: PRT
<213> ORGANISM: Mus musculus

<400> SEQUENCE: 5

Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
            20                  25                  30

Val Lys Pro Pro Thr Asn Lys Leu Pro Ile Phe Phe Phe Gly Thr His
        35                  40                  45

Glu Thr Ala Phe Leu Gly Pro Lys Asp Ile Phe Pro Tyr Ser Glu Asn
    50                  55                  60

Lys Glu Lys Tyr Gly Lys Pro Asn Lys Arg Lys Gly Phe Asn Glu Gly
65                  70                  75                  80

Leu Trp Glu Ile Asp Asn Asn Pro Lys Val Lys Phe Ser Ser Gln Gln
                85                  90                  95
```

Ala Ser Thr Lys Gln Ser Asn Ala Ser Ser Asp Val Glu Val Glu Glu
            100                 105                 110

Lys Glu Thr Asn Val Ser Lys Glu Asp Thr Asp Gln Glu
            115                 120                 125

<210> SEQ ID NO 6
<211> LENGTH: 123
<212> TYPE: PRT
<213> ORGANISM: Mus musculus

<400> SEQUENCE: 6

Met Ser Cys Phe Ser Arg Ser Lys Tyr Lys Thr Gly Asp Leu Val Phe
1               5                   10                  15

Ala Lys Leu Lys Gly Tyr Ala His Trp Pro Ala Arg Ile Glu His Val
            20                  25                  30

Ala Glu Ala Asn Arg Tyr Gln Val Phe Phe Gly Thr His Glu Thr
            35                  40                  45

Ala Leu Leu Gly Pro Arg His Leu Phe Pro Tyr Glu Glu Ser Lys Glu
        50                  55                  60

Lys Phe Gly Lys Pro Asn Lys Arg Arg Gly Phe Ser Glu Gly Leu Trp
65                  70                  75                  80

Glu Ile Glu His Asp Pro Met Val Glu Ala Ser Ser Leu Cys Ser
                85                  90                  95

Glu Glu Asp Gln Ser Tyr Thr Glu Asp Pro Gly Leu Ala Glu Glu Pro
            100                 105                 110

Glu Leu Gly Gln Glu Leu Val Gln Glu Leu Glu
            115                 120

<210> SEQ ID NO 7
<211> LENGTH: 121
<212> TYPE: PRT
<213> ORGANISM: Bos taurus

<400> SEQUENCE: 7

Met Ser Arg Phe Tyr Arg Arg Lys Tyr Lys Cys Gly Asp Leu Val Phe
1               5                   10                  15

Ala Lys Leu Lys Gly Tyr Ala His Trp Pro Ala Arg Ile Glu Gln Thr
            20                  25                  30

Ala Glu Ala Asn Arg Tyr Gln Val Phe Phe Gly Thr His Glu Thr
            35                  40                  45

Ala Phe Leu Gly Pro Arg His Leu Phe Pro Tyr Glu Glu Ser Lys Glu
        50                  55                  60

Lys Phe Gly Lys Pro Asn Lys Arg Arg Gly Phe Ser Glu Gly Leu Trp
65                  70                  75                  80

Glu Ile Glu Asn Asn Pro Thr Val Gln Ala Ser Asp Tyr Gln Cys Ala
                85                  90                  95

Leu Glu Lys Ser Cys Pro Glu Pro Glu Pro Glu Val Ala Glu Gly
            100                 105                 110

Gly Glu Asp Pro Lys Ser His Thr Asn
            115                 120

<210> SEQ ID NO 8
<211> LENGTH: 15
<212> TYPE: DNA
<213> ORGANISM: Artificial Sequence
<220> FEATURE:
<223> OTHER INFORMATION: synthetic oligonucleotide - designed Duplex DNA
      (Duplex 1)

-continued

```
<400> SEQUENCE: 8
tacaacaccc acaaa                                                    15

<210> SEQ ID NO 9
<211> LENGTH: 15
<212> TYPE: DNA
<213> ORGANISM: Artificial Sequence
<220> FEATURE:
<223> OTHER INFORMATION: synthetic oligonucleotide - designed Duplex DNA
      (Duplex 1)

<400> SEQUENCE: 9
tttgtgggtg ttgta                                                    15

<210> SEQ ID NO 10
<211> LENGTH: 15
<212> TYPE: DNA
<213> ORGANISM: Artificial Sequence
<220> FEATURE:
<223> OTHER INFORMATION: synthetic oligonucleotide - designed Duplex DNA
      (Duplex 2)

<400> SEQUENCE: 10
tacaacattc acaaa                                                    15

<210> SEQ ID NO 11
<211> LENGTH: 15
<212> TYPE: DNA
<213> ORGANISM: Artificial Sequence
<220> FEATURE:
<223> OTHER INFORMATION: synthetic oligonucleotide - designed Duplex DNA
      (Duplex 2)

<400> SEQUENCE: 11
tttgtgaatg ttgta                                                    15

<210> SEQ ID NO 12
<211> LENGTH: 17
<212> TYPE: DNA
<213> ORGANISM: Artificial Sequence
<220> FEATURE:
<223> OTHER INFORMATION: synthetic oligonucleotide - designed Duplex DNA
      (Duplex 3)

<400> SEQUENCE: 12
tacaacaaac ccacaaa                                                  17

<210> SEQ ID NO 13
<211> LENGTH: 15
<212> TYPE: DNA
<213> ORGANISM: Artificial Sequence
<220> FEATURE:
<223> OTHER INFORMATION: synthetic oligonucleotide - designed Duplex DNA
      (Duplex 3)

<400> SEQUENCE: 13
tttgtgggtg ttgta                                                    15

<210> SEQ ID NO 14
<211> LENGTH: 15
<212> TYPE: DNA
<213> ORGANISM: Artificial Sequence
<220> FEATURE:
<223> OTHER INFORMATION: synthetic oligonucleotide - designed Duplex DNA
      (Duplex 4)

<400> SEQUENCE: 14
```

```
cacacacaca cacac                                                      15

<210> SEQ ID NO 15
<211> LENGTH: 15
<212> TYPE: DNA
<213> ORGANISM: Artificial Sequence
<220> FEATURE:
<223> OTHER INFORMATION: synthetic oligonucleotide - designed Duplex DNA
      (Duplex 4)

<400> SEQUENCE: 15
gtgtgtgtgt gtgtg                                                      15

<210> SEQ ID NO 16
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 16
tacaacaccc acaaaaaatt tgtgggtgtt gta                                  33

<210> SEQ ID NO 17
<211> LENGTH: 33
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(33)
<223> OTHER INFORMATION: All nucleotides are 2'-OMe modified RNA
      nucleotides

<400> SEQUENCE: 17
uacaacaccc acaaaaaauu uguggguguu gua                                  33

<210> SEQ ID NO 18
<211> LENGTH: 32
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: b equals [CH2CH2O]5

<400> SEQUENCE: 18
tacaacaccc acaaabtttg tgggtgttgt ab                                   32

<210> SEQ ID NO 19
<211> LENGTH: 32
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: b is equal to [CH2CH2O]3

<400> SEQUENCE: 19
tacaacaccc acaaabtttg tgggtgttgt ab                                   32

<210> SEQ ID NO 20
<211> LENGTH: 33
<212> TYPE: DNA
<213> ORGANISM: Artificial Sequence
<220> FEATURE:
```

```
<223> OTHER INFORMATION: synthetic oligonucleotide
<220> FEATURE:
<221> NAME/KEY: misc_feature
<223> OTHER INFORMATION: Nucleotides 1 - 3, 16 - 18, and 31 - 33 are
      2'-OMe modified RNA nucleotides

<400> SEQUENCE: 20 uacaacacccc acaaaaaatt tgtgggtgtt gua                                33

<210> SEQ ID NO 21
<211> LENGTH: 33
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: Nucleotides 1 - 3 and 31 - 33 are 2'-OMe
      modified RNA nucleotides

<400> SEQUENCE: 21 uacaacacccc acaaaaaatt tgtgggtgtt gua                                33

<210> SEQ ID NO 22
<211> LENGTH: 33
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: Nucleotides 1 - 3, 15 - 19, and 31 - 33 are
      2'-OMe modified RNA nucleotides

<400> SEQUENCE: 22 uacaacacccc acaaaaaaut tgtgggtgtt gua                                33

<210> SEQ ID NO 23
<211> LENGTH: 34
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: b is a NH chemical moiety

<400> SEQUENCE: 23
btacaacacc cacaaaaaau ttgtgggtgt tgta                                34

<210> SEQ ID NO 24
<211> LENGTH: 34
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: b is equal to a PEG-NH chemical moiety
<220> FEATURE:
<221> NAME/KEY: misc_feature2
<222> LOCATION: (33)..(33)
<223> OTHER INFORMATION: Nucleotide 33 is a 2'-OMe modified RNA
      nucleotide

<400> SEQUENCE: 24
btacaacacc cacaaaaaau ttgtgggtgt tgta                                34

<210> SEQ ID NO 25
<211> LENGTH: 34
```

-continued

```
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: b is equal to a NH chemical moiety
<220> FEATURE:
<221> NAME/KEY: misc_feature2
<222> LOCATION: (33)..(33)
<223> OTHER INFORMATION: Nucleotide 33 is a 2'-OMe modified RNA
      nucleotide with an inversed polarity, i.e. a building block with a
      3'-3' inverted linkage

<400> SEQUENCE: 25
btacaacacc cacaaaaaau ttgtgggtgt tgta                                  34

<210> SEQ ID NO 26
<211> LENGTH: 34
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<223> OTHER INFORMATION: b is equal to a PEG(40kDa)-NH chemical moiety
<220> FEATURE:
<221> NAME/KEY: misc_feature2
<222> LOCATION: (15)..(19)
<223> OTHER INFORMATION: Nucleotides 15 - 19 are 2'-OMe modified RNA
      nucleotides
<220> FEATURE:
<221> NAME/KEY: misc_feature3
<222> LOCATION: (33)..(33)
<223> OTHER INFORMATION: Nucleotide 33 is a 2'-OMe modified RNA
      nucleotide with an inversed polarity, i.e. a building block with a
      3'-3' inverted linkage

<400> SEQUENCE: 26
btacaacacc cacaaaaaau ttgtgggtgt tgta                                  34
```